(12) United States Patent
Ding et al.

(10) Patent No.: US 11,318,069 B2
(45) Date of Patent: May 3, 2022

(54) DUAL CONTAINER SYSTEM FOR PRODUCT RECONSTITUTION

(71) Applicants: BAXTER INTERNATIONAL INC., Deerfield, IL (US); BAXTER HEALTHCARE SA, Glattpark (CH)

(72) Inventors: Yuanpang Samuel Ding, Long Grove, IL (US); Ying-Cheng Lo, Long Grove, IL (US); Jacob Daniel Rivett, Round Lake, IL (US); Grant Anthony Bomgaars, Kildeer, IL (US); Thomas Edward Dudar, Palatine, IL (US); Mark Edward Pasmore, Grayslake, IL (US); Michael Joseph Sadowski, Ringwood, IL (US); Anastasios Hristakos, Evanston, IL (US); Joseph Vincent Ranalletta, Greenville, SC (US); Bernd Krause, Rangendingen (DE)

(73) Assignees: BAXTER INTERNATIONAL INC., Deerfield, IL (US); BAXTER HEALTHCARE SA, Glattpark (CH)

(*) Notice: Subject to any disclaimer, the term of this patent is extended or adjusted under 35 U.S.C. 154(b) by 89 days.

(21) Appl. No.: 16/630,994

(22) PCT Filed: Jul. 12, 2018

(86) PCT No.: PCT/US2018/041801
§ 371 (c)(1),
(2) Date: Jan. 14, 2020

(87) PCT Pub. No.: WO2019/018198
PCT Pub. Date: Jan. 24, 2019

(65) Prior Publication Data
US 2020/0214938 A1 Jul. 9, 2020

Related U.S. Application Data

(60) Provisional application No. 62/533,380, filed on Jul. 17, 2017.

(51) Int. Cl.
*A61J 1/20* (2006.01)
*A61J 1/10* (2006.01)
(Continued)

(52) U.S. Cl.
CPC ............... *A61J 1/2089* (2013.01); *A61J 1/10* (2013.01); *A61J 1/2048* (2015.05); *A61J 1/2086* (2015.05);
(Continued)

(58) Field of Classification Search
CPC ...... A61J 1/2089; A61J 1/2048; A61J 1/2086; A61J 1/2013; A61J 1/2096
See application file for complete search history.

(56) References Cited

U.S. PATENT DOCUMENTS

| | | |
|---|---|---|
| 4,265,760 A | 5/1981 | Abel et al. |
| 4,372,100 A | 2/1983 | Miller et al. |

(Continued)

FOREIGN PATENT DOCUMENTS

EP 0522107 B1 12/1995

OTHER PUBLICATIONS

International Application No. PCT/US2018/041801, International Search Report and Written Opinion, dated Sep. 10, 2018.
(Continued)

*Primary Examiner* — Timothy P. Kelly
(74) *Attorney, Agent, or Firm* — Marshall, Gerstein & Borun LLP

(57) ABSTRACT

A system for reconstituting and sterilizing a concentrate includes a mixing container, a filtration device, and a prod-
(Continued)

uct bag. The a mixing container has an inlet port and outlet port in fluid communication with a mixing chamber disposed between the inlet port and the outlet port. The mixing chamber is adapted to contain a product concentrate. The filtration device has an inlet and an outlet, the inlet of the filtration device coupled to the outlet port of the mixing container. The filtration device includes a filter membrane with a nominal pore size in a range of approximately 0.1 µm to approximately 0.5 µm. The product bag has an inlet port coupled to the outlet of the filtration device, and has a bladder defining an empty sterile chamber for receiving sterilized and reconstituted product resulting from mixing a diluent with a product concentrate in the mixing chamber to obtain a mixture then introduced through the filtration device to obtain the reconstituted and sterilized product.

20 Claims, 14 Drawing Sheets

(51) Int. Cl.
*A61M 5/31* (2006.01)
*B01D 69/06* (2006.01)
*B01D 69/08* (2006.01)

(52) U.S. Cl.
CPC .......... *A61M 5/3129* (2013.01); *B01D 69/06* (2013.01); *B01D 69/08* (2013.01)

(56) References Cited

U.S. PATENT DOCUMENTS

| | | | |
|---|---|---|---|
| 5,490,848 A * | 2/1996 | Finley | A61J 1/2089 604/403 |
| 2007/0079894 A1 * | 4/2007 | Kraus | A61J 1/2072 141/319 |
| 2011/0178493 A1 * | 7/2011 | Okiyama | A61J 1/2089 604/406 |
| 2015/0283032 A1 | 10/2015 | Lin et al. | |
| 2016/0206512 A1 * | 7/2016 | Chhikara | A61J 1/22 |
| 2020/0222281 A1 * | 7/2020 | Ding | A61J 1/1456 |

OTHER PUBLICATIONS

Written Opinion for International Application No. PCT/US2018/041801, dated Sep. 10, 2018.
International Search Report for International Application No. PCT/US2018/041801, dated Sep. 10, 2018.
European Patent Application No. 18746547.1, Communication Pursuant to Article 94(3) EPC, dated Mar. 1, 2021.

* cited by examiner

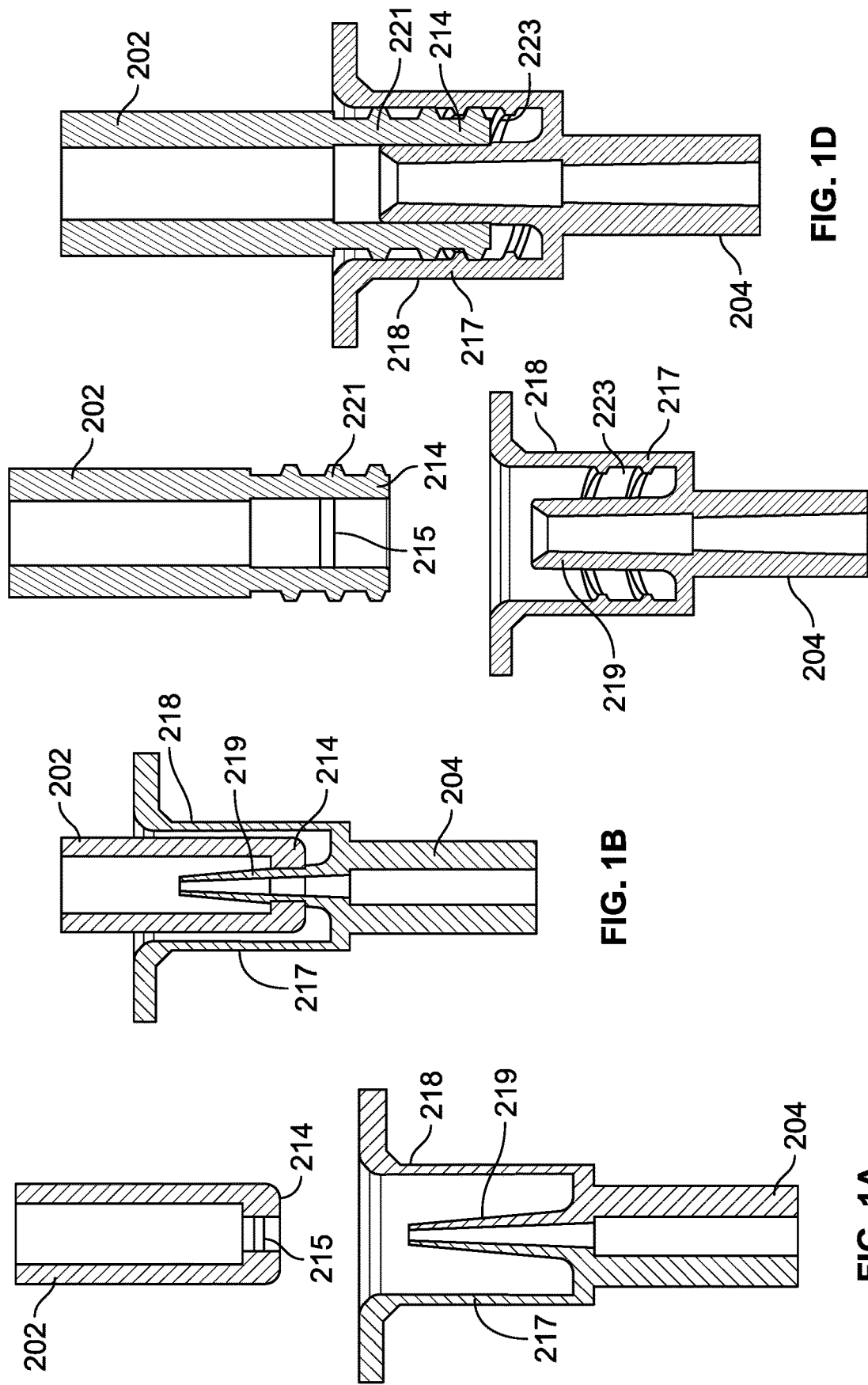

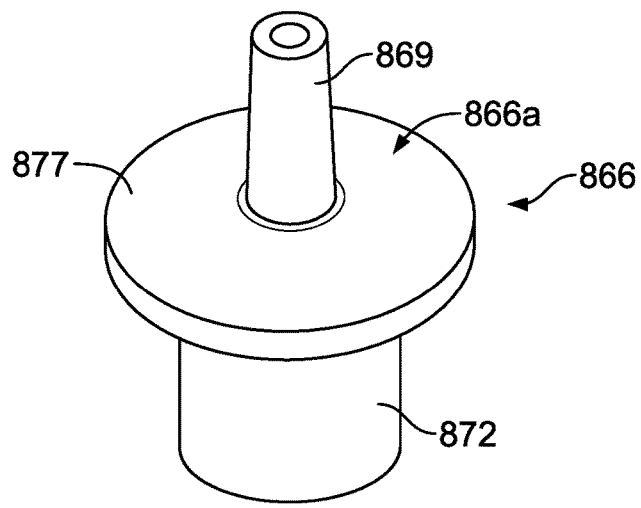
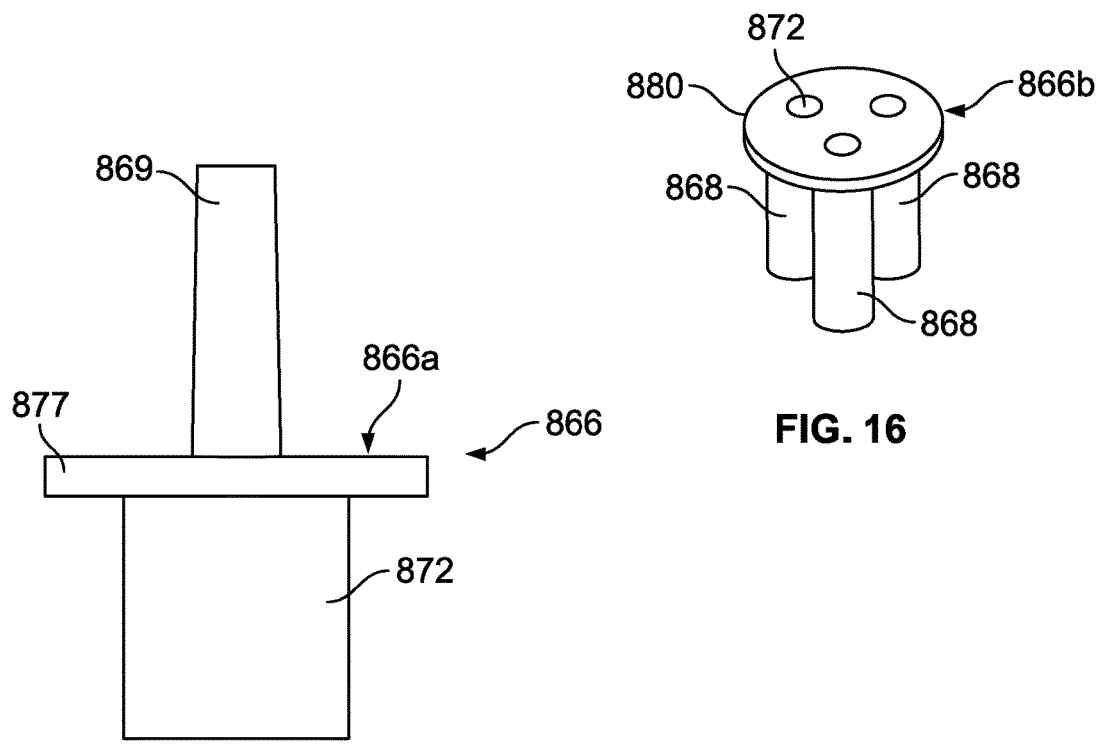
FIG. 16
FIG. 17

DUAL CONTAINER SYSTEM FOR PRODUCT RECONSTITUTION

CROSS-REFERENCE TO AND RELATED APPLICATIONS

This is the United States national phase of International Patent Application No. PCT/US18/41801, filed Jul. 12, 2018, which application claims priority U.S. Provisional Application Ser. No. 62/533,380, filed Jul. 17, 2017, the entire contents of each of which are incorporated herein by reference.

Additionally, the following related and co-owned applications are hereby expressly incorporated herein by reference in their entirety: U.S. Provisional Application Ser. No. 62/533,362, (entitled STERILE PRODUCT BAG WITH FILTERED PORT); U.S. Provisional Application Ser. No. 62/533,408, (entitled MEDICAL PRODUCT INCLUDING PRE-FILLED PRODUCT BAG WITH FILTERED FLUID PORT); U.S. Provisional Application Ser. No. 62/533,427, (entitled FILTERED PRODUCT BAG WITH COMPACT FORM FACTOR); and U.S. Provisional Application Ser. No. 62/533,440, (entitled MEDICAL SYRINGE SYSTEM WITH FILTERED FILLING PORT), each filed on Jul. 17, 2017.

FIELD OF THE DISCLOSURE

This disclosure relates to a system for reconstituting a concentrate and, more particularly, a dual container system for reconstituting and sterilizing a non-sterile concentrate.

BACKGROUND

Often, drugs and nutrients are mixed with a pharmaceutical fluid such as a diluent before being delivered to a patient. The diluent may be, for example, a dextrose solution, a saline solution or even water. Many such drugs or nutrients are supplied in a concentrated form such as powder, liquid, gel, foam, etc., and packaged in glass or plastic vials.

In order for the concentrate to be administered to a patient, it must first undergo reconstitution. As used herein, the term reconstitution includes not only liquidization of non-liquid concentrates but also dilution of liquid concentrates.

One way of reconstituting a concentrate is first to inject a diluent into the vial holding the concentrate. This may typically be performed by a syringe having a liquid diluent contained in the syringe barrel. After the rubber stopper of the vial is pierced by the syringe needle, the liquid is injected into the vial. The vial is shaken to reconstitute and dilute the concentrate with the liquid. The liquid is then withdrawn back into the syringe. These steps may be repeated several times to ensure complete reconstitution of the concentrate. After the final mixing, the syringe is withdrawn and the reconstituted product may then be injected into a medication port of a parenteral solution container (e.g., an IV bag) containing a medical solution or diluent such as dextrose or saline solution. The drug, now diluted with the medical solution in the parenteral solution container, is delivered through an administration set for intravenous administration to the patient.

Some known parenteral solution containers have even been developed to include a device for connecting directly to the vial, thereby bypassing the need for the syringe. Such devices utilize a cannula extending from the parenteral container and with a sharp exterior end sealed inside of a sheath with a removable closure. When reconstitution is required, the removable closure can be removed and a vial containing concentrate is pierced with the sharp end of the cannula to provide for fluid communication back and forth between the vial and the interior chamber of the parenteral container. This allows the user to mix the component and ultimately store them in the parenteral container for administration to the patient.

Due to the necessity for only sterile solutions being delivered to patients, the drug or nutrient concentrate and even the pharmaceutical fluid used for reconstitution must be sterile prior to, during, and after reconstitution is performed. Thus whether the drug or nutrient is reconstituted and added to an IV bag using a syringe or vial attachment prior to administration, the steps to reconstitute and add should be undertaken in a manner and in an environment to reduce the potential of contamination. For example, frequently these steps are undertaken within a laminar flow fume hood found in the pharmacy. Although these hoods may offer an effective amount of space, there is still a general hindrance in undertaking the reconstitution and addition and also the risk of contamination cannot be completely removed. If the steps are undertaken in other areas of the health care setting, the risk of contamination may be even greater.

Moreover, the drug or nutrient and the containers in which they reside are typically provided to hospitals or pharmacists, for example, pre-filled and pre-sterilized. For concentrates, these must be either filled into their containers in an aseptic environment and/or filled and subsequently sterilized. Aseptic filling can be tedious, costly, and time consuming. While sterilizing filled containers can be cost effective, certain drugs can be sensitive to heat and therefore steam sterilization is not an option. Other forms of sterilization can be much more costly and time consuming. Aseptic filling can also pose a risk that the concentrate is not at desired level of sterility prior to reconstitution and addition to the IV bag.

SUMMARY

One aspect of the present disclosure provides a system for reconstituting and sterilizing a concentrate includes a mixing container, a filtration device, and a product bag. The a mixing container has an inlet port and outlet port in fluid communication with a mixing chamber disposed between the inlet port and the outlet port. The mixing chamber is adapted to contain a product concentrate. The filtration device has an inlet and an outlet, the inlet of the filtration device coupled to the outlet port of the mixing container. The filtration device includes a filter membrane with a nominal pore size in a range of approximately 0.1 µm to approximately 0.5 µm. The product bag has an inlet port coupled to the outlet of the filtration device, and has a bladder defining an empty sterile chamber for receiving sterilized and reconstituted product resulting from mixing a pharmaceutical fluid with a product concentrate in the mixing chamber to obtain a mixture then introduced through the filtration device to obtain the reconstituted and sterilized product.

In some aspects, the system also includes a product concentrate disposed in the mixing chamber.

In some aspects, the product concentrate in the mixing chamber is a non-sterile product concentrate.

In some aspects, the filter membrane is shaped as (a) a hollow fiber with a wall and pores residing in the wall of the fiber, or (b) a flat filter disposed within a rectangular, square or box-like filter housing, the flat filter having a wall and pores residing in the wall.

In some aspects, the filtration device comprises a stem and the filter membrane is disposed in line with the stem between the inlet and outlet of the filtration device.

In some aspects, the stem defines a seal-and-cut area between the filter membrane and the inlet port of the product bag, the seal-and-cut area adapted to allow the stem to be sealed and cut to close the inlet port of the product bag.

In some aspects, the filter membrane comprises a plurality of filter membranes.

In some aspects, the filter membrane includes an inlet end and an outlet end, wherein the outlet end is sealed and the inlet end is an open inlet.

In some aspects, the filter membrane has a wall thickness in the range of approximately 150 μm to approximately 500 μm.

In some aspects, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In some aspects, the stem is one of a flexible stem or a rigid stem.

In some aspects, the stem is made of at least one of the following materials: PVC, PET, a poly(meth)acrylate, a polycarbonate, a polyolefin, a cycloolefin copolymer, polystyrene, or a silicone polymer.

In some aspects, the filter membrane includes at least one U-shaped hollow fiber filter membrane secured in a U-shaped configuration by a filter membrane housing contained within a filter body.

In some aspects, the filter membrane includes a plurality of U-shaped hollow fiber filter membranes.

In some aspects, the filter membrane comprises a plurality of parallel hollow fiber membrane filters secured in a side-by-side configuration.

In some aspects, the filter membrane comprises a plurality of parallel hollow fiber membrane filters arranged in a circular pattern.

In some aspects, the filter membrane has a nominal pore size in a range of approximately 0.1 μm to approximately 0.22 μm.

In some aspects, the non-sterile product concentrate comprises a medicinal or nutritional concentrate disposed.

In some aspects, the mixing container comprises a drip chamber with two open ends, one of the open ends being the inlet port for receiving a diluent.

In some aspects, the mixing container comprises a vial with two open ends, one of the open ends being the inlet port for receiving a diluent.

In some aspects, wherein the mixing container comprises a bag defining the inlet port adapted to receive a diluent.

In some aspects, the mixing container comprises a vial with a single open end, and the system further comprises a vial adaptor defining the inlet port and outlet port, the vial adaptor further defining a mixing port coupled to the single open end of the vial.

In some aspects, the vial adaptor further comprises a first conduit establishing fluid communication between the inlet port and the mixing port, and a second conduit establishing fluid communication between the mixing port and the outlet port.

In some aspects, each of the first and second conduits includes a terminal end that is disposed within the vial, the terminal end of the first conduit extending further into the vial than the second terminal end.

In some aspects, the product bag further comprises an administration port separate from the inlet port of the product bag for facilitating administration of the reconstituted and sterilized product to a patient.

Another aspect of the present disclosure provides a system for reconstituting a non-sterile concentrate, wherein the system includes a mixing container, a non-sterile concentrate, and a filtration device. The mixing container has an inlet port and outlet port in fluid communication with a non-sterile mixing chamber disposed between the inlet port and the outlet port. The non-sterile product concentrate is disposed in the mixing chamber. The filtration device has an inlet and an outlet, the inlet of the filtration device coupled to the outlet port of the mixing container. The filtration device also having a filter membrane disposed between the inlet and outlet of the filtration device and having a nominal pore size in a range of approximately 0.1 μm to approximately 0.5 μm, for producing sterilized and reconstituted product resulting from mixing a pharmaceutical fluid with the non-sterile product concentrate in the mixing chamber to obtain a non-sterile mixture then introduced through the filtration device to obtain the reconstituted and sterilized product.

In some aspects, the system also includes a product bag having an inlet port adapted to be coupled to the outlet of the filtration device, the product bag having a bladder defining an empty sterile chamber for receiving the reconstituted and sterilized product from the outlet of the filtration device.

In some aspect, the system further includes a syringe with a delivery end adapted to be coupled to the outlet of the filtration device, the syringe having a syringe barrel defining a reservoir, a plunger, and a stopper slidably disposed in the reservoir, the reservoir defining an empty sterile chamber for receiving the reconstituted and sterilized product from the outlet of the filtration device.

In some aspects, the filter membrane is shaped as (a) a hollow fiber with a wall and pores residing in the wall of the fiber, or (b) a flat filter disposed within a rectangular, square or box-like filter housing, the flat filter having a wall and pores residing in the wall In some aspects, the filtration device comprises a stem and the filter membrane is disposed in line with the stem.

In some aspects, the stem defines a seal-and-cut area between the filter membrane and the inlet port of the product bag, the seal-and-cut area adapted to allow the stem to be sealed and cut to close the inlet port of the product bag.

In some aspects, the filter membrane comprises a plurality of filter membranes.

In some aspects, the filter membrane includes an inlet end and an outlet end, wherein the outlet end is sealed and the inlet end is an open inlet.

In some aspects, the filter membrane has a wall thickness in the range of approximately 150 μm to approximately 500 μm.

In some aspects, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In some aspects, the stem is one of a flexible stem or a rigid stem.

In some aspects, the stem is made of at least one of the following materials: PVC, PET, a poly(meth)acrylate, a polycarbonate, a polyolefin, a cycloolefin copolymer, polystyrene, or a silicone polymer.

In some aspects, the filter membrane includes at least one U-shaped hollow fiber filter membrane secured in a U-shaped configuration by a filter membrane housing contained within a filter body.

In some aspects, the filter membrane includes a plurality of U-shaped hollow fiber filter membranes.

In some aspects, the filter membrane comprises a plurality of parallel hollow fiber membrane filters secured in a side-by-side configuration.

In some aspects, the filter membrane comprises a plurality of parallel hollow fiber membrane filters arranged in a circular pattern.

In some aspects, the filter membrane has a nominal pore size in a range of approximately 0.1 μm to approximately 0.22 μm.

In some aspects, the non-sterile product concentrate comprises a medicinal or nutritional concentrate disposed.

In some aspects, the mixing container comprises a drip chamber with two open ends, one of the open ends being the inlet port for receiving a diluent.

In some aspects, the mixing container comprises a vial with two open ends, one of the open ends being the inlet port for receiving a diluent.

In some aspects, the mixing container comprises a bag defining the inlet port adapted to receive a diluent.

In some aspects, the mixing container comprises a vial with a single open end, and the system further comprises a vial adaptor defining the inlet port and outlet port, the vial adaptor further defining a mixing port coupled to the single open end of the vial.

In some aspects, the vial adaptor further comprises a first conduit establishing fluid communication between the inlet port and the mixing port, and a second conduit establishing fluid communication between the mixing port and the outlet port.

In some aspects, each of the first and second conduits includes a terminal end that is disposed within the vial, the terminal end of the first conduit extending further into the vial than the second terminal end.

In some aspects, the product bag further comprises an administration port separate from the inlet port of the product bag for facilitating administration of the reconstituted and sterilized product to a patient.

Yet another aspect of the present disclosure provides a method of reconstituting and sterilizing a concentrate. The method includes providing a mixing container having an inlet port and outlet port in fluid communication with a non-sterile mixing chamber disposed between the inlet port and the outlet port, a non-sterile product concentrate disposed in the mixing chamber, and a filtration device having an inlet and an outlet, the inlet of the filtration device coupled to the outlet port of the mixing container, the filtration device comprising a filter membrane disposed between the inlet and outlet of the filtration device and having a nominal pore size in a range of approximately 0.1 μm to approximately 0.5 μm. The method also includes introducing a pharmaceutical fluid into the mixing chamber through the inlet port of the mixing container. The method also includes mixing the pharmaceutical fluid and concentrate to obtain non-sterile reconstituted product. The method also includes passing the reconstituted product through the outlet port of the mixing chamber and through the filtration device to obtain sterilized and reconstituted product.

In some aspects, the method also includes providing a product bag having an inlet port coupled to the outlet of the filtration device, the product bag having a bladder defining an empty sterile chamber, and introducing the sterilized and reconstituted product into the sterile chamber of the product bag from the outlet of the filtration device.

In some aspects, the method further includes providing a syringe with a delivery end adapted to be coupled to the outlet of the filtration device, the syringe having a syringe barrel defining a reservoir, a plunger, and a stopper slidably disposed in the reservoir, the reservoir defining an empty sterile chamber; and introducing the sterilized and reconstituted product into the sterile chamber of the syringe from the outlet of the filtration device.

In some aspects, passing the non-sterile reconstituted product through the filtration device comprises passing the non-sterile reconstituted product through a plurality of filter membranes.

In some aspects, passing the non-sterile reconstituted product through the filtration device comprises passing the non-sterile reconstituted product through an open outlet end and a sealed outlet end of the hollow fiber of the filter membrane.

In some aspects, passing the non-sterile reconstituted product through the filtration device comprises passing the non-sterile reconstituted product through a filter membrane having a wall thickness in the range of approximately 150 μm to approximately 500 μm.

In some aspects, passing the non-sterile reconstituted product through the filtration device comprises passing the non-sterile reconstituted product through a filter membrane having a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In some aspects, passing the non-sterile reconstituted product through the filtration device comprises passing the non-sterile reconstituted product through a filter membrane made of at least one of the following materials: a polyolefin, polyvinylidene fluoride, polymethylmethacrylate, polyacrylonitrile, polysulfone, polyethersulfone, and a polymer containing cationic charges.

In some aspects, passing the non-sterile reconstituted product through the filtration device comprises passing the non-sterile reconstituted product through a filter having at least one U-shaped hollow fiber filter membrane secured in a U-shaped configuration by a filter membrane housing contained within a filter body.

In some aspects, passing non-sterile reconstituted product through a filter having at least one U-shaped hollow fiber filter membrane comprises passing the non-sterile reconstituted product through a plurality of U-shaped hollow fiber filter membranes.

In some aspects, passing the non-sterile reconstituted product through the filtration device comprises passing the non-sterile reconstituted product through a plurality of parallel hollow fiber membrane filters secured in a side-by-side configuration.

In some aspects, passing the non-sterile reconstituted product through the filtration device comprises passing the non-sterile reconstituted product through a plurality of parallel hollow fiber membrane filters arranged in a circular pattern.

In some aspects, passing the non-sterile reconstituted product through the filtration device comprises passing the non-sterile reconstituted product through a filter membrane having a nominal pore size in a range of approximately 0.1 µm to approximately 0.22 µm.

In some aspects, the method further includes sealing and cutting the filtration device at a location between the filter membrane and the inlet port of the product bag to close the inlet port of the product bag.

In some aspects, the method further includes performing a filter integrity test on the filter.

In some aspects, the method further includes removing the filtration device from the mixing container prior to performing the filter integrity test.

In some aspects, performing the filter integrity test comprises one of a pressure degradation test, a bubble point test, a water intrusion test, or a water flow test.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 1A is an exploded cross-sectional side view of one version of a removable attachment between a mixing container and a filtration device of the system of FIG. 1;

FIG. 1B is an assembled cross-sectional side view of the removable attachment of FIG. 1A;

FIG. 1C is an exploded cross-sectional side view of an alternative version of a removable attachment between a mixing container and a filtration device of the system of FIG. 1;

FIG. 1D is an assembled cross-sectional side view of the removable attachment of FIG. 1C;

FIG. 16 is an exploded perspective view of an alternative connector for use with a three-filter filter bundle;

FIG. 17 is a side exploded view of the connector of FIG. 16;

DETAILED DESCRIPTION

The present disclosure is directed to a novel system and method for reconstituting a product concentrate, which can be sterile or non-sterile, and subsequently passing the resultant product through a sterilizing filter. Generally, the system includes a mixing container that stores the optionally non-sterile product concentrate such as a drug or nutrient in the form of a powder, a gel, a foam, a liquid, etc. The mixing container includes an inlet port adapted to receive a diluent, and an outlet port coupled to an inlet of a sterilization filtration device. In one embodiment, the outlet of the filtration device is coupled to a product bag with a pre-sterilized inner chamber such that sterilized product departing the filtration device flows into the product bag for subsequent storage and administration. One benefit of this arrangement is that the product concentrate need not be stored in the mixing container in a sterile condition, or while the concentrate can be introduced into the mixing container in a sterile condition, there is less importance on the need to maintain and/or monitor that sterility throughout shipping and storage. Another advantage is that this arrangement allows for reconstitution to be performed on-demand at a hospital or pharmacy, for example. That is, the system can be provided containing only the product concentrate. A pharmacist can introduce a diluent to reconstitute the product in the mixing container, which is then pushed through the sterilization filter to result in a sterile product ready for patient administration. This on-demand process greatly reduces the risk of pre-sterilized products becoming contaminated, and also reduces the cost of managing and verifying sterile materials, as well as shipping heavy pre-filled bags of pre-sterilized pharmaceutical fluid.

Figure 2:
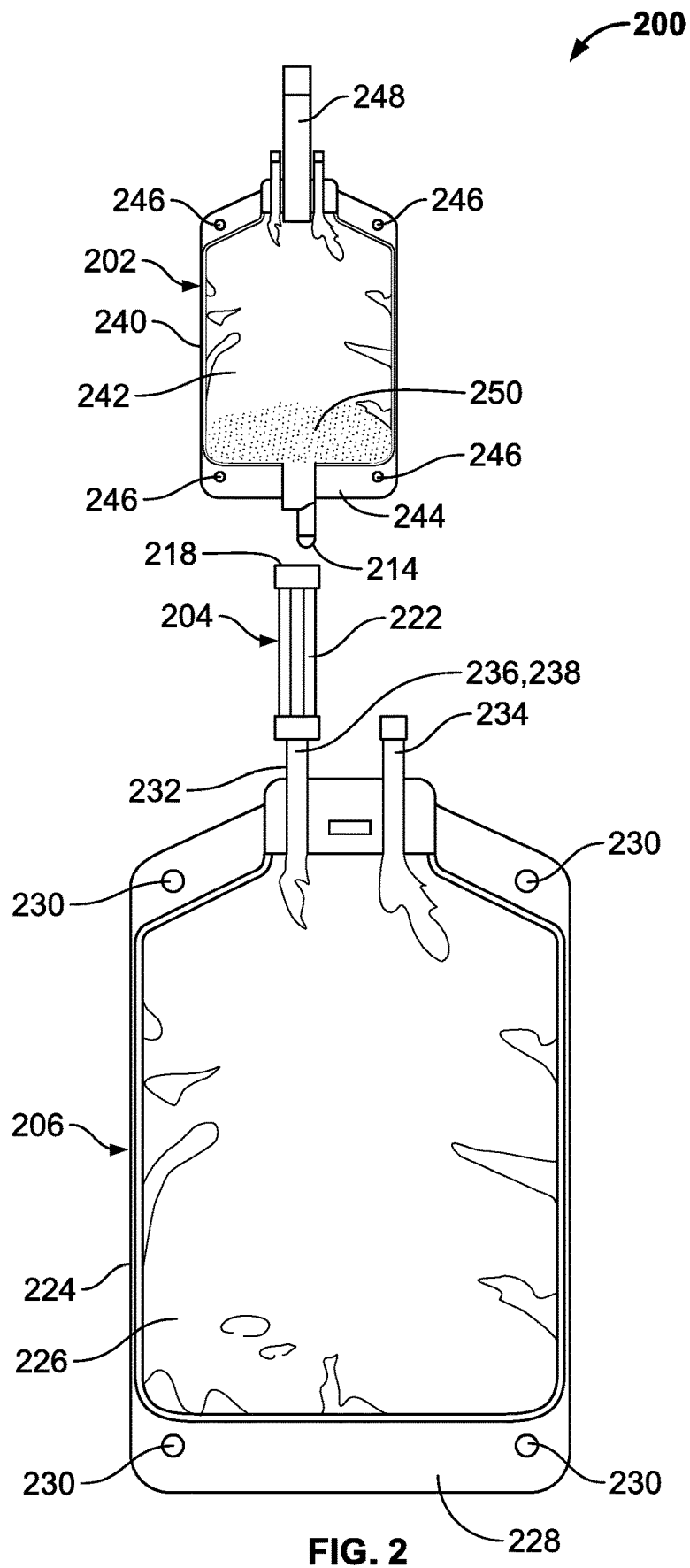
FIG. 2 is a front view of a second embodiment of a dual container system for reconstituting and sterilizing a concentrate in accordance with the present disclosure.
Figure 3:
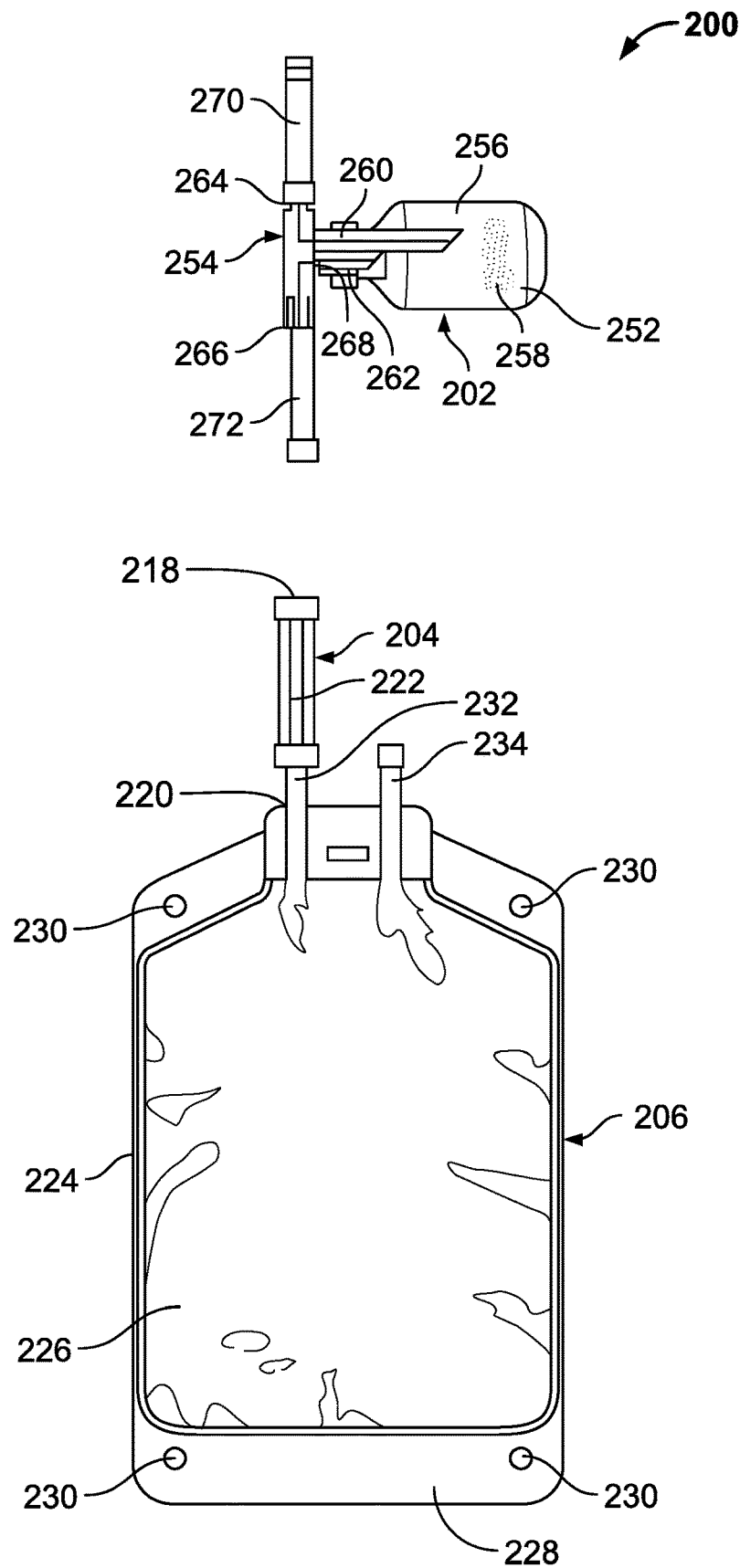
FIG. 3 is a front view, partially in cross-section, of a third embodiment of a dual container system for reconstituting and sterilizing a concentrate in accordance with the present disclosure.
Figure 21:
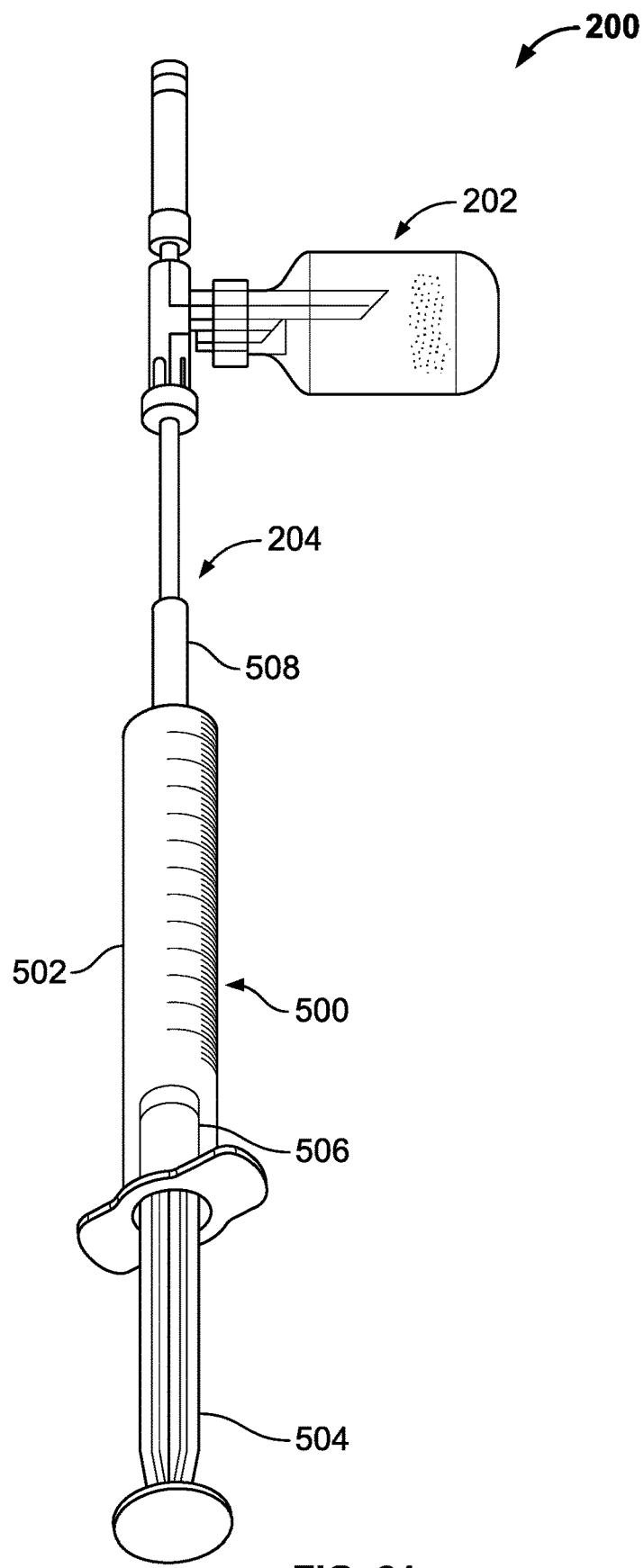
FIG. 21 is a front view, partially in cross-section, of an alternative version of the dual container system of FIG. 3.

To meet the foregoing, the present disclosure provides multiple embodiments of reconstitution and sterilization systems. A first embodiment described primarily with reference to FIG. 1 includes a mixing container in the form of a simple drip chamber or two open ended vial. FIG. 2 includes a mixing container in the form of a medical bag. FIGS. 3 and 21 each includes a mixing chamber that embodies a conventional drug vial. While the mixing containers can vary, each embodiment shares a common and unique technical features and principle of operation.

Figure 1:
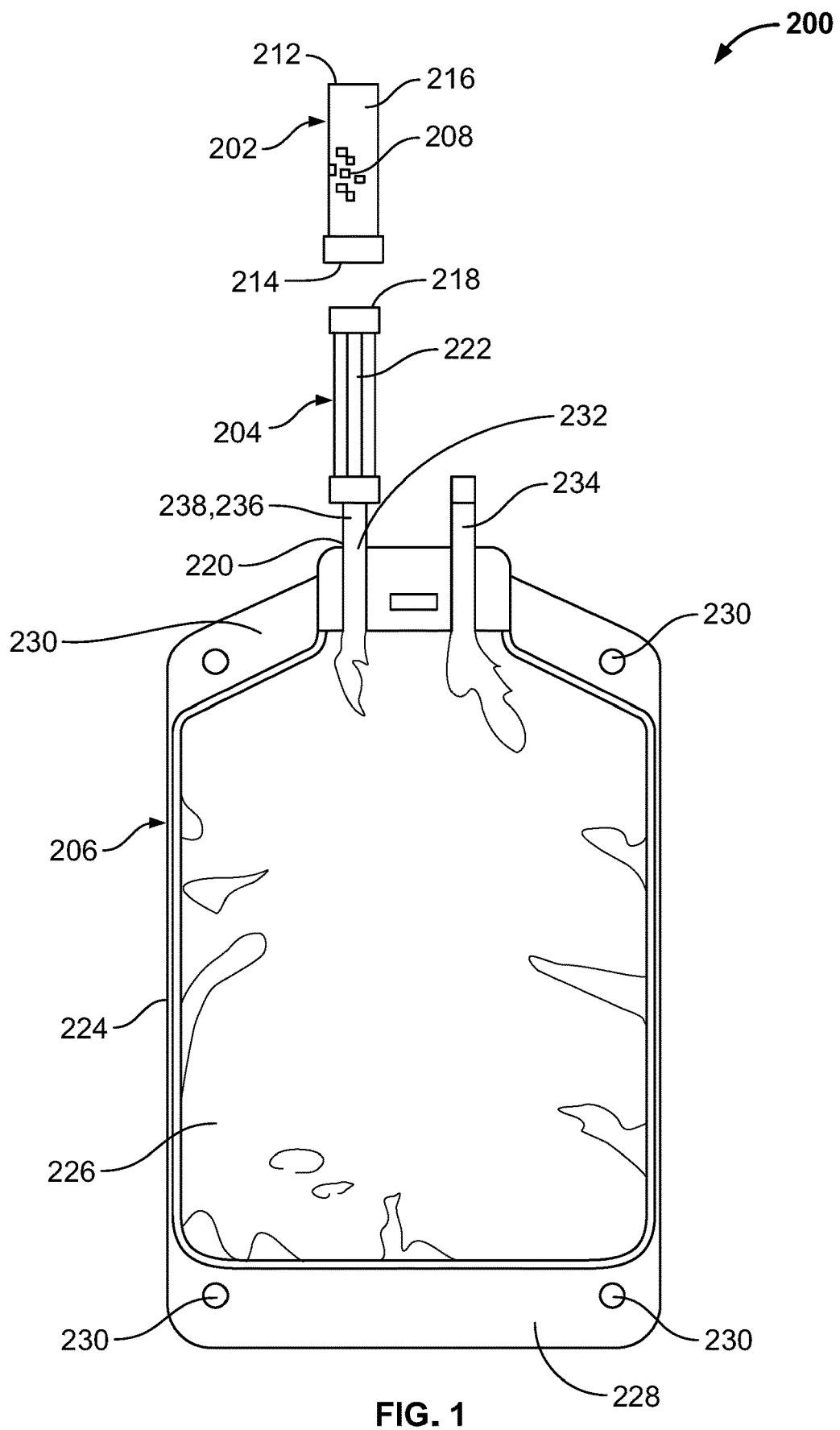
FIG. 1 is a front view of a first embodiment of a dual container system for reconstituting and sterilizing a concentrate in accordance with the present disclosure.

FIG. 1 illustrates a first embodiment of a system 200 for reconstituting and sterilizing a product concentrate in accordance with the present disclosure. The system 200 includes a mixing container 202, a product bag 206, and a filtration device 204 coupled between the mixing container 202 and product bag 204. As shown in FIG. 1, in some versions the mixing container 202 is a separate container adapted to be connected to and also removable from the filtration device 204, as will be discussed below. In other versions, the mixing container 202 can be provided pre-attached to the filtration device 204.

The mixing container 202, as shown, contains a volume of a product concentrate 208. The product concentrate 208 can include a drug concentrate or a nutrient concentrate, for example, and may be in the form of a powder, a liquid, a gel, a foam, or any other concentrated form requiring reconstitution prior to patient administration. As mentioned, in some embodiments, the concentrate 208 can be sterile or non-sterile. The filtration device 204 includes an inlet 218, an outlet 220, and a filter membrane 222 disposed between the inlet and outlet 218, 220. The product bag 206 includes a generally conventional medical bag constructed of medical grade films to define a bladder 224 that is a fillable pouch having a sterile interior chamber 226 with a standard volume capacity. The chamber 226 can be sterilized through any known means such as steam sterilization, Gamma irradiation, etc. At least partially surrounding a perimeter of the bladder 224 is a sealed perimeter 228 having a plurality of apertures 230 configured to receive mounting hang pins during filling, administration, and/or storage. The chamber 226 of the bladder 224 is fluidly connected to an inlet port 232 of the bladder 206. An administration port 234 is disposed on the bladder 206 for being coupled to an administration set to facilitate patient administration. Other ports can be included as desired.

Still referring to FIG. 1, the mixing container 202 of the present embodiment can include a drip chamber or a glass vial 216 having an inlet port 212, an outlet port 214, and a mixing chamber 216 between the inlet and outlet ports 212, 214. In some versions, the inlet port 212 can include a septum or other piercable membrane. The mixing chamber 216 as well as the product concentrate 208 stored in the mixing chamber 216 can be non-sterile or sterile. The outlet port 214 of the mixing container 202 is coupled, preferably directly, to the inlet 218 of the filtration device 204. The outlet 220 of the filtration device 220 is coupled, preferably directly, to the inlet port 232 of the product bag 206.

As mentioned briefly above, in some embodiments, the outlet port 214 of the mixing container 202 can be permanently attached to the inlet 218 of the filtration device 204. In other embodiments, the outlet port 214 of the mixing container 202 can be removably attached to the inlet 218 of the filtration device 204 in order to facilitate a filter integrity test, as will be described below. For example, FIGS. 1A-1D depict two different possible coupling mechanisms for removably attaching and detaching the mixing container 202 to the filtration device 204. In FIGS. 1A and 1B, the outlet port 214 of the mixing container 202 can include a piercable diaphragm or septum 215 and the inlet 218 of the filtration device can include a shroud 217 and piercing member 219. So configured, the outlet port 214 can be brought into contact with the inlet 218 of the filtration device 204 such that the piercing member 219 pierces the diaphragm or septum 215 to establish a fluid pathway between the mixing container 202 and the filtration device 204, as shown in FIG. 1B. In some versions, the connection between mixing container 202 and the filtration device 204 shown in FIG. 1B can be maintained with friction present between the outlet port 214 and the shroud 217, between the outlet port 214 and the piercing member 219, between the outlet port 214 and the diaphragm or septum 215, or some other means. Thus, to detach the mixing container 202 from the filtration device 204, a simple axial force may be applied to overcome the friction fit. For example, FIGS. 1C and 1D illustrate an alternative, similar to FIGS. 1A and 1B, but where the mixing container 202 and filtration device 204 are attached and detached through a threaded connection. Specifically, as shown, the outlet port 214 of the mixing container 202 can have external threads 221 and the shroud 217 of the filtration device 204 can have internal threads 223 that threadably engage the external threads 221. So configured, when attaching the mixing container 202 to the filtration device 204, the piercing member 219 penetrates the diaphragm or septum 215 and relative rotation of the mixing container 202 and filtration device 204 cause the internal and external threads 221, 223 to engage, thereby attaching the components together. Thus, to detach the mixing container 202 from the filtration device 204, opposite relative rotation can unthread the outlet port 214 from the inlet 218.

Referring back to FIG. 1, when the system 200 is fully assembled, a pharmaceutical fluid such as a water, saline, a solution, a diluent, etc. used for reconstituting concentrates can be introduced into the inlet port 212 of the mixing chamber 202 to mix with the product concentrate 208. Because the mixture will subsequently be passed through a sterilizing filter, the pharmaceutical fluid can be sterile or non-sterile. The user may take certain actions (e.g., shaking, swirling, rocking, etc.) to facilitate mixing the fluid and the concentrate in the mixing chamber 216 while additional fluid is introduced into the mixing chamber 216 to begin forcing the mixture out of the mixing container 202 and through the filtration device 204. As the mixture flows into the filtration device 204, the mixture filters through the filter membrane 222, resulting in a sterilized and reconstituted product flowing out of the outlet 220 of the filtration device 204 and into the product bag 206.

In some embodiments, the filtration device 204, as shown in FIG. 1, includes a stem 236, in line with which the filter membrane 222 is mounted. In the version of FIG. 1, the stem 236 is shown as only extending below the filter membrane 222, but in other versions, the stem 236 may also extend above the filter membrane 222 and/or the filter membrane 222 may be physically disposed inside of the stem 236. Regardless, the stem 236 in FIG. 1 is located between the filter membrane 222 and the inlet port 232 of the product bag 206 and constitutes an essentially hollow conduit region defining a "seal and cut area". The phrase "seal and cut area" pertains to the manner in which the product bags are sealed and cut after introducing fluid to the chamber 226 through the filtration device 204. That is, the disclosed arrangement is designed such that after the product bag 206 receives the reconstituted and sterilized product from the filtration device 222, a sealing mechanism can be employed to seal the stem 236 closed in the "seal and cut area," which is below the filter membrane 222 but above the inlet port 232 of the product bag 206. Thus, the "seal and cut area" 238 in this version is a portion of the stem 236 above the product bag 206 where the filter membrane 222 does not reside. Sealing of the "seal and cut area" 238 can be achieved with a heat sealer or any other device, including for example clamping a clamp onto the "seal and cut area" 238. Once the stem 236 is sealed, the stem 236 is cut at a location above the seal but below the filter membrane 222. Cutting may be achieved with a knife or any other device. The stem 236 provides an isolated fluid connection between the inlet 232 and the chamber 226 of the bladder 224 of the product bag 206, such that once the product is filtered through the filter membrane 222, the reconstituted and sterilized product passes directly into the sterilized environment of the empty chamber 226 of the bag 206. Hence, after the bag 206 receives the reconstituted and sterilized product and the stem 236 is sealed and cut, the reconstituted and sterilized product in the bladder 226 remains sterile until the bladder 224 is punctured or compromised. This, of course, assumes that the filtration device 204 was uncompromised prior to filling and performed as desired.

To ensure that the filter membrane 222 performed properly, a filter integrity test can be performed. A filter integrity test is facilitated by the arrangement of the "seal and cut area" 238 of the stem 236, which allows for the filter membrane 222 to be separated intact from the remainder of the now-sealed product bag 206. For example, after the stem 236 and filter membrane 222 are separated from the product bag 206, a filter testing device (not shown) may be pre-programmed or controlled to perform a filter integrity test on the filter membrane 222. Examples of filter integrity tests might include a bubble point test, a pressure degradation test, a water intrusion test, a water flow test, or any suitable test known in the art. A pressure degradation test is a method for testing the quality of a filter either before or after the filter has been used. In the preferred embodiment, the filter membrane 222 is tested after the mixture passes through the filter membrane 222 and into the product bag 206. To perform the filter integrity test using a pressure degradation test procedure, the filtration device 204 not only removed from the product bag 206, but also preferably removed from the mixing container 202. For example, the outlet port 214 of the mixing container 202 can be removably attached to the inlet 218 of the filtration device in the manners described above with respect to FIGS. 1A-1D and, as such, the mixing container 202 can easily be removed from the filtration device 204 prior to performing the filter integrity test. Thus, with the mixing container 202 detached, a test head (not shown) applies an air pressure of a predetermined value to the inlet 218 and filtration device 204. In one embodiment, the pre-determined value is the pressure where gas cannot permeate the filter membrane 222 of an acceptable filtration device 204. A pressure sensor, or other method of measuring the integrity of the filter, is located within the test head and measures the pressure decay or diffusion rate through the filter membrane 222. The results from the integrity test are assessed to determine the quality of the filter membrane 222, and therefore the quality of the solution that previously passed through the filter membrane 222 and into the product bag 206. If the pressure sensor measures a decay or a unexpected rate of decay, then the filtration device 204 fails the test and it can be determined that the solution in the product bag is unsatisfactory. Alternatively in a bubble point test, the test head gradually increases the pressure applied to the filter membrane 222, and the increase in pressure is measured in parallel with the diffusion rate of the gas through the filter membrane 222. Any disproportionate increase in diffusion rate in relation to the applied pressure may indicate a hole or other structural flaw in the filter membrane 222, and the filter would fail the integrity test.

Thus, it can be appreciated that the disclosed arrangement of the "seal and cut area" 238 disclosed herein advantageously facilitates the filter integrity test, and a determination that the fluid in the product bag is either sterile or has the potential of being compromised may be made with a high degree of certainty.

FIG. 2 depicts a second embodiment of a system 200 for reconstituting and sterilizing concentrate in accordance with the teachings of the present disclosure. Like the system of FIG. 1, the system of FIG. 2 includes a mixing container 202, a product bag 206, and a filtration device coupled between the mixing container 202 and product bag 206. Same as that described above, the mixing container 202 includes an outlet port 214 that can be either permanently attached or removably attached to the inlet 218 of the filtration device 204 using one of the connections described in FIGS. 1A-1D or any other suitable connection. The filtration device 204 and product bag 206 in FIG. 2 are identical to the same components in FIG. 1, so the details will not be repeated. The mixing container 202, however, is distinct from that described with reference to FIG. 1.

In FIG. 2, the mixing container 202 includes a construct similar to the product bag 206 in that it is constructed of medical grade films to define a bladder 240 that is a fillable pouch having an interior chamber 242 with a standard volume capacity. And, in the interior chamber 242, resides a volume of a product concentrate 250. In contrast to the product bag 206, the chamber 242 of the mixing container 202 need not be sterile. In fact, both the chamber 242 and the concentrate 250 disposed in the chamber 242 can be non-sterile or sterile in accordance with the teachings and benefits of the present disclosure. At least partially surrounding a perimeter of the bladder 240 is a sealed perimeter 244 having a plurality of apertures 246 configured to receive mounting hang pins during filling, administration, and/or storage. The chamber 242 of the bladder 240 is fluidly connected to an inlet port 248 of the bladder 240. The inlet port 248 may be an open port or may include a septum or membrane that is adapted to be pierced by a filling nozzle during a filling operation, for example. Additional ports or openings may also be provided, as depicted, such as a pair of medicine ports for introducing additional fluids as may be desired.

From the foregoing, it should be appreciate that the process for reconstituting and sterilizing the non-sterile product concentrate 250 in the system 200 of FIG. 2 is substantially identical to the process described above with respect to FIG. 1. As such, the details will not be repeated. One difference in the process may include the fact that the mixing container 202 in FIG. 2 is a flexible bag, which lends itself to manual manipulation. As such, as a pharmaceutical fluid is introduced into the chamber 242 through the inlet port 248, the user may manually manipulate and/or massage the bladder 240 to facilitate mixing of the pharmaceutical fluid and concentrate 250 prior to passing the mixture through the filtration device 204.

FIG. 3 depicts a third embodiment of a system 200 for reconstituting and sterilizing concentrate in accordance with the teachings of the present disclosure. Like the system of FIGS. 1 and 2, the system of FIG. 3 includes a mixing container 202, a product bag 206, and a filtration device 204 coupled between the mixing container 202 and product bag 206. Same as that described above with respect to FIGS. 1 and 2, the mixing container 202 includes an outlet port 214 that can be either permanently attached or removably attached to the inlet 218 of the filtration device 204 using one of the connections described in FIGS. 1A-1D or any other suitable connection. The filtration device 204 and product bag 206 in FIG. 3 are identical to the same components in FIGS. 1 and 2, so the details will not be repeated. The details of the mixing container 202, however, are distinct from that described with reference to FIGS. 1 and 2.

In FIG. 3, the mixing container 202 includes a traditional vial 252 in combination with a vial adaptor 254. The vial 252 defines an interior chamber 256 containing a volume of a product concentrate 258, and an opening 260, which can include a rubber stopper 262 or other fitment for attaching to the vial adaptor 254, as will be described. As with prior embodiments, the chamber 256 of the mixing container 202 of FIG. 3 need not be sterile. In fact, both the chamber 256 and the concentrate 258 disposed in the chamber 256 can be non-sterile or sterile in accordance with the teachings and benefits of the present disclosure.

Figure 3A:
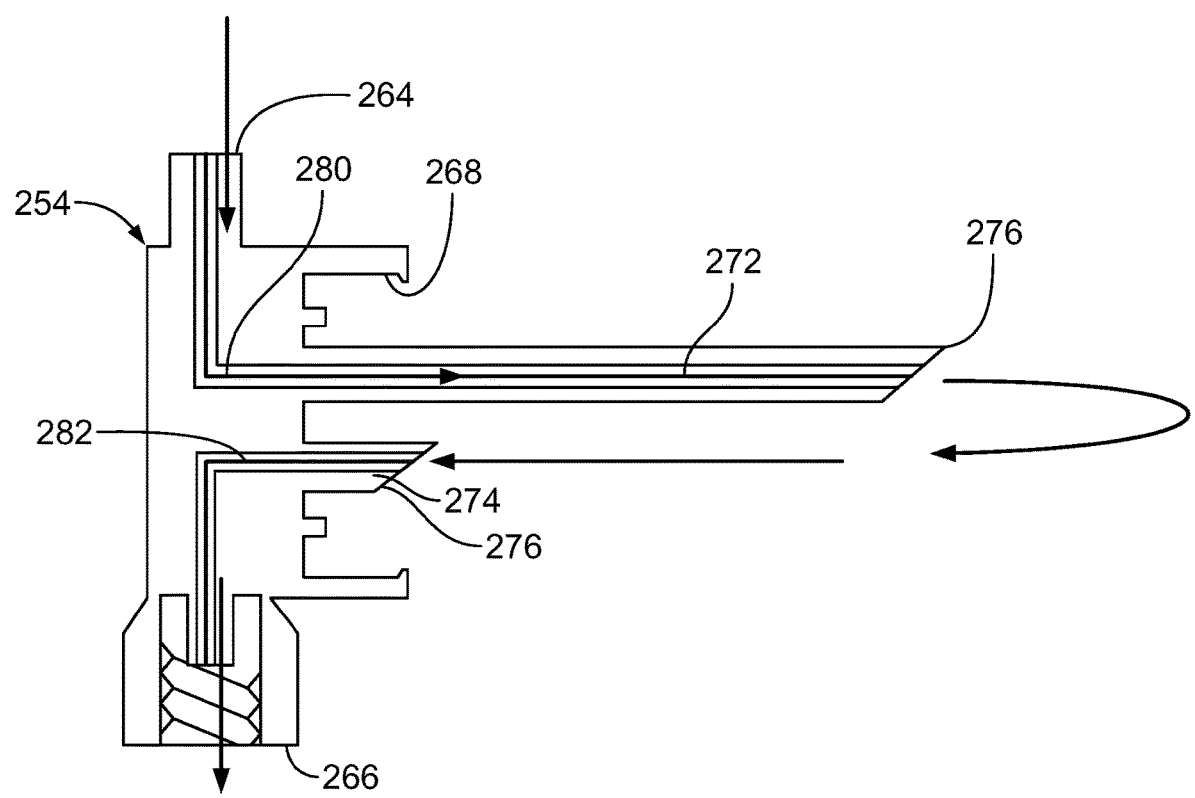
FIG. 3A is a schematic cross-sectional detail of a vial adaptor of FIG. 3.

As seen in FIGS. 3 and 3A, the vial adaptor 254 includes a T-shaped connector including an inlet port 264, an outlet port 266, and a mixing port 268. The mixing port 268 is connected to the vial 252 and, more particularly, the opening 260 of the vial 252. In the version of FIG. 3, the inlet port 264 of the vial adaptor 254 is connected to a first fill tube 270 and the outlet port 266 is connected to a second fill tube 272. The first and second fill tubes 270, 272 can be threadably or otherwise connected to the inlet and outlet ports 264, 266, respectively. An opposite end of the second fill tube 272 is also connected to the inlet 218 of the filtration device 204. In some embodiments, the second fill tube 272 can be removably attached to the inlet 218 of the filtration device 204 such as to facilitate removal of the mixing container for performing a filter integrity test. In some embodiments, the second fill tube 272 can be removably attached to the filtration device 204 using one of the connections described in FIGS. 1A-1D or any other suitable connection. In other embodiments, the vial adaptor 254 could be provided without either or both of the fill tubes 270, 272 such that, in some versions, the outlet port 266 is connected directly to the inlet 218 of the filtration device 204. In that case, the outlet port 266 can be removably attached to the filtration device 204 using one of the connections described in FIGS. 1A-1D or any other suitable connection.

Figure 4:
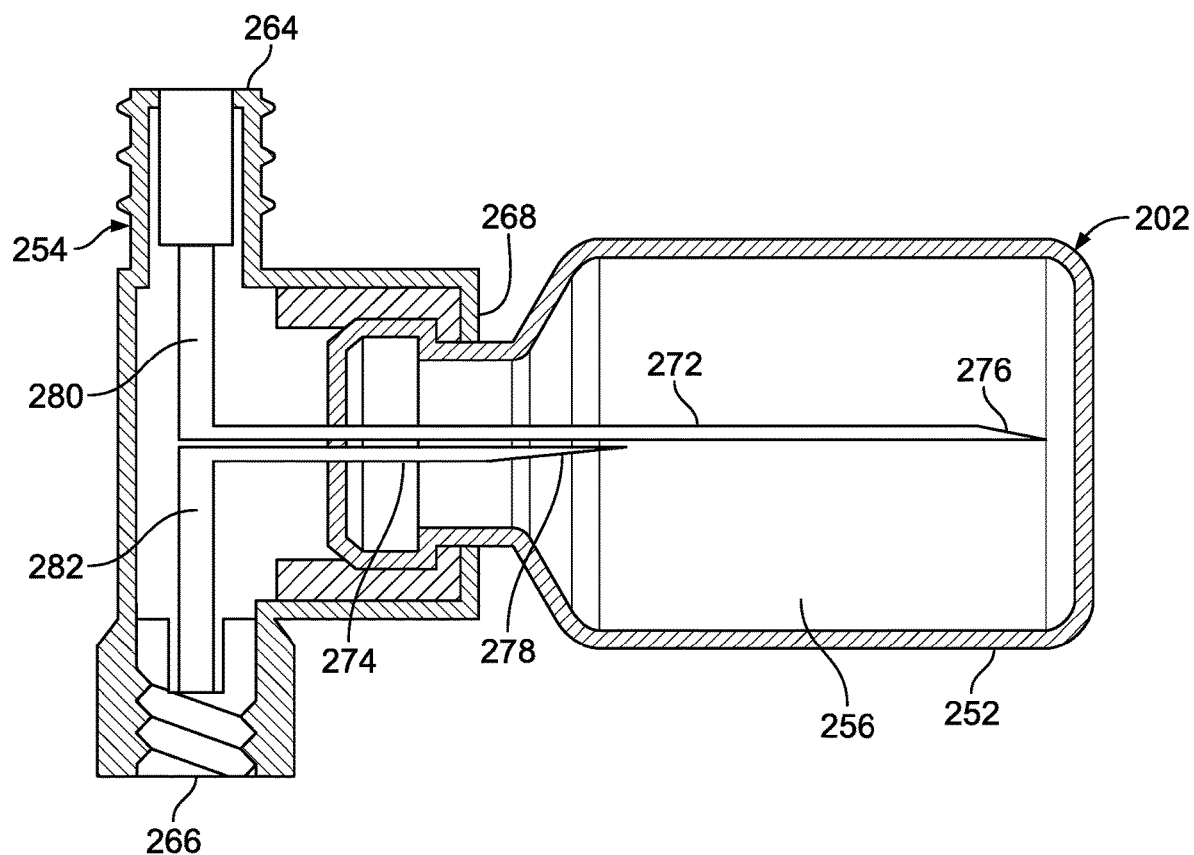
FIG. 4 is a cross-sectional detail view of the vial adaptor of FIG. 3 connected to an associated vial.

As shown in more detail in FIG. 3A, the mixing port 268 of the vial adaptor 254 further includes a first conduit 272 and a second conduit 274, which as depicted in FIG. 4, assist with flowing fluid through the mixing container 202 during use. Specifically, as depicted in FIG. 4, the first conduit 272 includes a terminal end 276 and the second conduit 274 includes a terminal end 278, each terminal end 276, 278 disposed inside of the chamber 256 of the vial 252. In this version, the terminal end 276 of the first conduit 272 extends further into the chamber 256 than the terminal end 278 of the second conduit 274 for facilitating mixing and reducing the potential for backflow during use because as oriented during use, the first conduit 272 is positioned above the second conduit 274 in the direction of gravity. That is, during use, the vial 252 would most likely be oriented "upside down" such that the rubber stopper of the vial 252 would be at the bottom, so the conduits 272, 274 extend generally upward. In this configuration, the terminal end 276 of the first conduit 272 is located above the terminal end 278 of the second conduct 274 such that the terminal end 278 of the second conduit 274 is located at the bottom of the vial 252 to facilitate the drainage of the drug solution into the final product bag 206. With the vial adaptor 254 configured as described, it can be seen in FIG. 3A, that the adaptor 254 defines in inlet flow path 280 and an outlet flow path 282. The inlet flow path 280 begins at the inlet port 265 and flows to the terminal end 276 of the first conduit 272. The outlet flow path 282 begins at the terminal end 278 of the second conduit 274 and flows to the outlet port 266.

From the foregoing, it should be appreciate that the process for reconstituting and sterilizing the product concentrate 258 in the system 200 of FIG. 3 is substantially identical to the process described above with respect to FIGS. 1 and 2. As such, the details will not be repeated. The primary distinction would be that the pharmaceutical fluid passing through the inlet port 264 of the vial adaptor 254 and into the vial 252 must flow through the first flow path 280, which includes in the depicted version one ninety-degree turn. Similarly, the mixture leaving the vial 252 through the mixing port 268 of the vial adaptor 254 must flow through the second flow path 282, which also includes in the depicted version one ninety-degree turn. The structure of these flow paths and rigidity of the vial 252 may benefit from the user manually manipulating the vial 252 to facilitate mixing of the pharmaceutical fluid and concentrate 258 in a manner similar to that described with reference to the mixing container 202 of FIG. 1. While the adaptor 254 of the disclosed version is T-shaped and includes conduits 280, 282 with ninety-degree turns, other versions of the adaptor 254 are contemplated.

As mentioned, during use of the foregoing systems 200, a pharmacist or other technician must introduce a pharmaceutical fluid such as a diluent into the mixing container 202 to begin reconstituting the product concentrate. This can be accomplished manually, automatically, or semi-automatically.

As mentioned, each of the foregoing embodiments includes a filtration device 204 for sterilizing the mixture of concentrate and pharmaceutical fluid before the mixture reaches the product bag 206. While each of the foregoing embodiments includes a product bag 206 coupled to the outlet 220 of the filtration device 204, in other versions of the present disclosure, the system 200 does not require the product bag 206. In such versions, the outlet 220 of the filtration device 204 can be adapted to be connected to a different storage facility, an administration set for direct patient administration, or otherwise. As such, it should be understood that in the present disclosure of the system 200, the product bag 206 is an optional aspect.

For example, FIG. 21 depicts one alternative version of the system 200 described above with reference to FIG. 3 for reconstituting and sterilizing concentrate in accordance with the teachings of the present disclosure. Like the system of FIG. 3, the system in FIG. 21 includes a mixing container 202 and a filtration device 204. Distinct, however, is that the system 200 in FIG. 21 does not include a product bag 206. Instead, it includes a syringe 500 on the receiving end of the filtration device 204. The syringe 500 can be generally conventional and include a syringe barrel 502 defining a cavity or reservoir, a plunger 504 connected to a stopper 506 disposed in the cavity or reservoir, and a delivery end 508. As shown, the delivery end 508 of the syringe 500 is connected to the filtration device 204. All other aspects, structural and functional, of the mixing container 202 and filtration device 204 in FIG. 21 can be identical to those described in reference to FIGS. 3-4 and, as such, the details will not be repeated. So configured, one the reconstituted product has been sufficiently delivered into the syringe 500, the mixing container 202 can be removed from the filtration device 204, and the filtration device can be removed from the delivery end 508 of the syringe 500 for integrity testing.

Then, the product in the syringe 500 can be delivered to a patient with a needle through an administration set or other means as is generally known.

Figure 5:
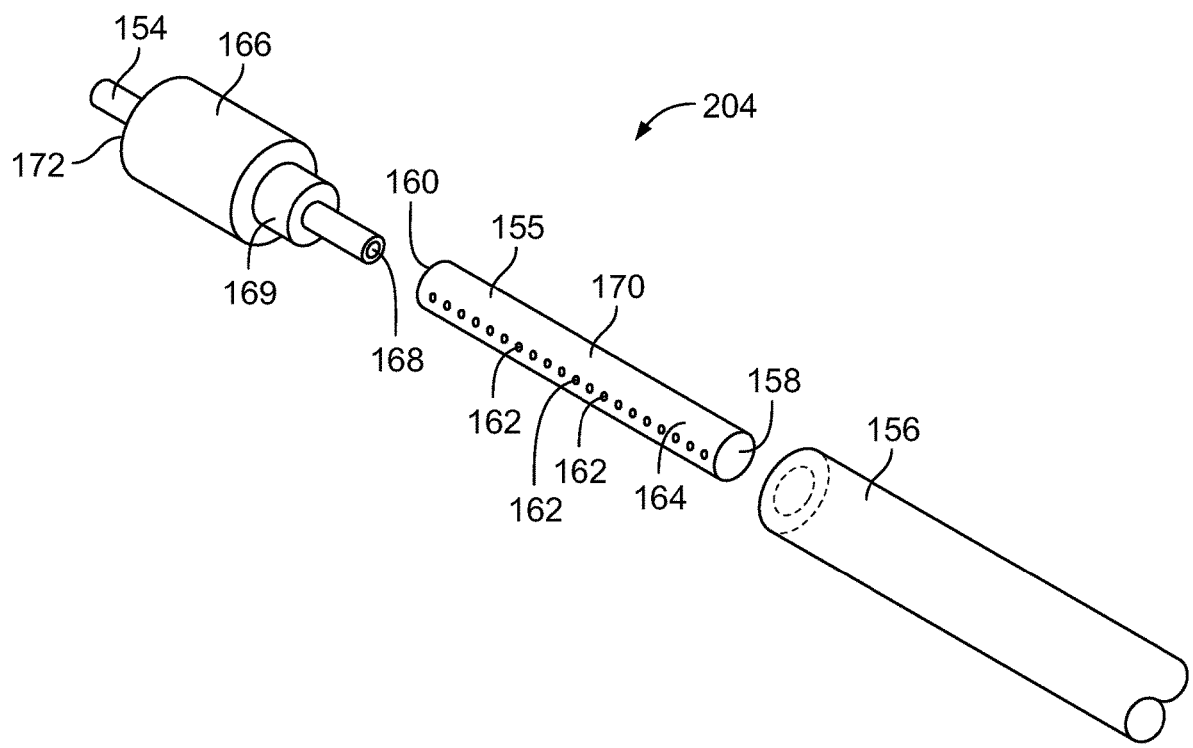
FIG. 5 is an expanded isometric view of one embodiment of a filtration device for use with the system of any one of FIGS. 1-3.
Figure 6:
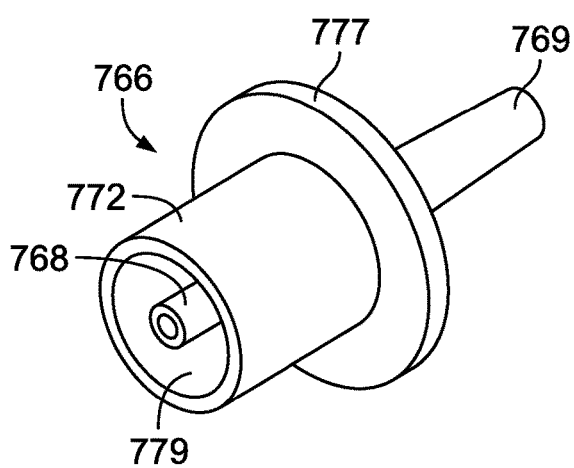
FIG. 6 is a perspective view of an alternative connector for use with the filtration device of FIG. 5.
Figure 7:
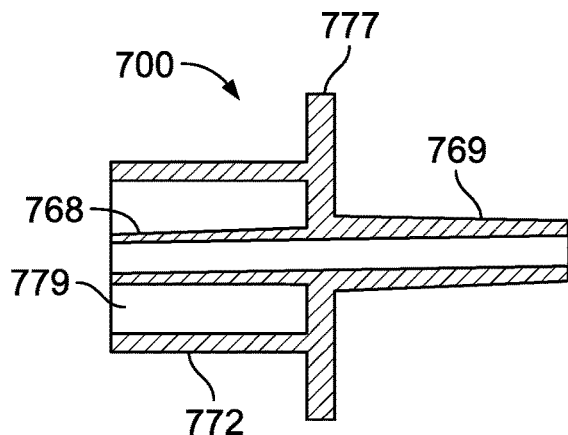
FIG. 7 is a side cross-sectional view of the connector of FIG. 6.
Figure 8:
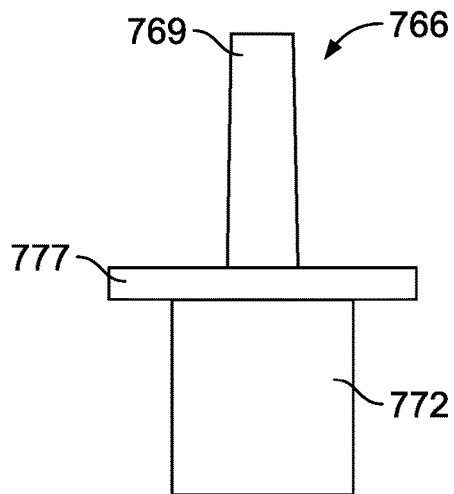
FIG. 8 is a side view of the connector of FIG. 6.
Figure 9:
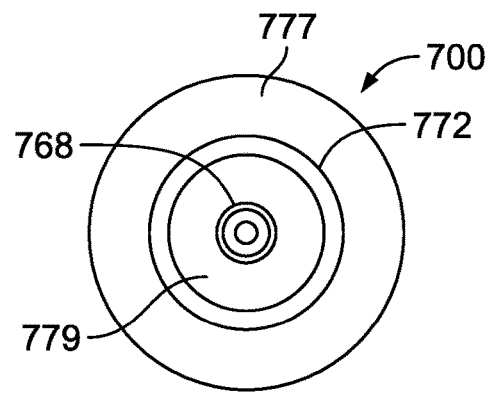
FIG. 9 is a bottom view of the connector of FIG. 8.
Figure 10:
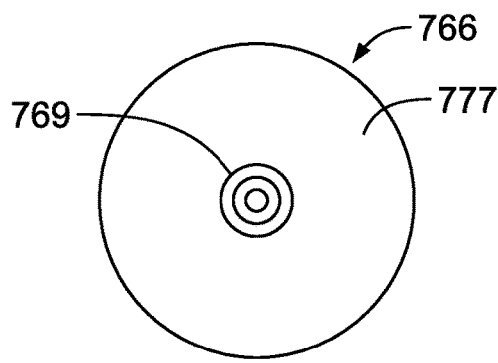
FIG. 10 is a top view of the connector of FIG. 8.

As described, the filtration device 204 of the systems 200 include a filter membrane 222. The filter membrane 222 can take various forms to achieve the intended sterilization. For example, as shown in FIG. 5, one embodiment of a filtration device 204. While all of the reference numerals used in FIG. 5 do not directly correlate to those used in FIGS. 1-3 and 21, it should be appreciated that the filtration device 204 in FIGS. 1-3 and 21 can be embodied by the filtration device 204 of FIG. 5. In FIG. 5, the filtration device 204 has a filter 155 that can be a hollow fiber membrane with one sealed end 158 and one open inlet end 160. The sealed end 158 can be capped or it may be sealed with a heat seal, an adhesive, or some other means. A plurality of pores 162 along the surface 164 of the filter 155 allow a pharmaceutical fluid that entered the filter 155 at the open inlet end 160 to exit the filter 155. In one version, the stem 156 surrounds the filter membrane 170 in a generally concentric configuration so filtered pharmaceutical fluid exiting the filter membrane 170 is contained within the stem 156 and ultimately passed, in some embodiments, to the product bag 206.

As depicted in FIG. 5, a hollow connector 166 can be used to secure the stem 156 and the filter 155 together. The open inlet end 160 of the filter 155 is sealingly connected to an open outlet end 168 of the hollow connector 166. The connection may be achieved by gluing the open inlet end 160 of the filter 155 to the open outlet end 168 of the connector 166 with, for example, an epoxy resin, a polyurethane resin, a cyanoacrylate resin, a UV curing acrylic adhesive, or a solvent for the material of the hollow connector 166 such as cyclohexanone. In the version depicted, the open outlet end 168 of the connector 166 comprises a hollow cylindrical member that fits inside of and is fixed to the open inlet end 160 of the filter 155. As such, an outer diameter of the open outlet end 168 of the connector 166 is substantially similar to or slightly smaller than an inner diameter of the open inlet end 160 of the filter 155. In some versions, the open inlet end 160 of the filter 155 may be welded to the open outlet end 168 of the connector 166 by, for example, heat welding (e.g., introducing a hot conical metal tip into the open inlet end 150 of the filter 155 to partially melt it), laser welding if the hollow connector 166 is made from a material that absorbs laser radiation, mirror welding, ultrasound welding, and friction welding. Alternately, the filter 155 may be inserted into a mold, and a thermoplastic polymer may be injection-molded around it to form the hollow connector 166. Other designs and configurations for connecting the filter 155 to the connector 166 are intended to be within the scope of the present disclosure.

The hollow connector 166 further includes a fluid inlet 169 for connecting to the outlet port 214 of the mixing container 202 of any of FIGS. 1-3 and 21, for example. In some versions, the fluid inlet 169 can include a Luer type fitting or other standard medical fitting. The mixture from the mixing container 202 can then travel through the hollow connector 166 and exit into the filter 155 through the open outlet end 168 of the hollow connector 166. The hollow connector 166 also includes a sealing surface 172 to which the stem 156 is attached. The sealing surface 172 in this version is cylindrical and has a diameter larger than a diameter of the open outlet end 168, and is disposed generally concentric with the open outlet end 168. In fact, in this version, the outer diameter of the sealing surface 172 is generally identical to or slightly smaller than an inner diameter of the stem 156. So configured, the stem 156 receives the sealing surface 172 and extends therefrom to surround and protect the filter 155 without contacting the surface 164 of the filter 155. The stem 156 can be fixed to the sealing surface 172 with adhesive (e.g., a UV curing acrylic adhesive), epoxy, welding, bonding, etc. The stem 156 receives the pharmaceutical solution after it passes through the pores 162 in the filter 155. From there, the now filtered solution passes into the bladder 152.

FIGS. 6-10 illustrate an alternative hollow connector 766, similar to connector 166, for securing the stem 156 and the hollow fiber filter 155 of FIG. 5 together. The connector 766 includes an open outlet end 768 carried by a stem structure that extends in a first direction from a bearing plate 777 and is adapted to be sealingly connected to the open inlet end 160 of the filter 155. The connection may be achieved by gluing the open inlet end 160 of the filter 155 to the open outlet end 768 of the connector 766 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet end 768 of the connector 766 comprises a hollow cylindrical member that fits inside of and is fixed to the open inlet end 160 of the filter 155. As such, an outer diameter of the open outlet end 768 of the connector 766 is substantially similar to or slightly smaller than an inner diameter of the open inlet end 160 of the filter 155. In some versions, the open inlet end 160 of the filter 155 may be welded to the open outlet end 768 of the connector 766 by, for example, heat welding (e.g., introducing a hot conical metal tip into the open inlet end 150 of the filter 155 to partially melt it), laser welding if the hollow connector 766 is made from a material that absorbs laser radiation, mirror welding, ultrasound welding, and friction welding. Alternately, the filter 155 may be inserted into a mold, and a thermoplastic polymer may be injection-molded around it to form the hollow connector 766. Other designs and configurations for connecting the filter 155 to the connector 766 are intended to be within the scope of the present disclosure.

The hollow connector 766 further includes a fluid inlet 769, which is also a stem structure, extending in a second direction (opposite the first direction) from the bearing plate 777. The fluid inlet 769 of the hollow connector 766 is adapted to connect to the outlet port 214 of the mixing container 202 of FIGS. 1-3 and 21, for example. In some versions, the fluid inlet 769 can include a Luer type fitting or other standard medical fitting. The mixture from the mixing container 202 can then travel through the hollow connector 766 and exit into the filter 155 through the open outlet end 768 of the hollow connector 766.

The hollow connector 766 also includes a sealing surface 772 to which the stem 156 is attached. The sealing surface 772 in this version is a cylindrical shroud extending from the bearing plate 777 in the first direction and has a diameter larger than a diameter of the open outlet end 768. The sealing surface 772 is disposed generally concentric with the open outlet end 768. As such, in this embodiment, the shroud of the sealing surface 772 surrounds the stem structure of the open outlet end 768 such that an annular gap 779 resides between the two. In fact, in this version, the outer diameter of the sealing surface 772 is generally identical to or slightly smaller than an inner diameter of the stem 156. So configured, the sealing surface 772 of the connector 766 can be received by the stem 156 such that the stem 156 extends therefrom to surround and protect the filter 155 without contacting the surface 164 of the filter 155. The stem 156 can be fixed to the sealing surface 772 with adhesive (e.g., a UV curing acrylic adhesive), epoxy, welding, bonding, etc. The stem 156 receives the mixture after it passes through the pores 162 in the filter 155. From there, the now filtered product passes, in come embodiments, to the product bag 206.

While the foregoing version of the filtration device 204 has been described as including a single filter membrane 170, in other embodiments within the scope of the present disclosure, the filtration device 204 may include multiple filter membranes 170. A few non-limiting examples of multiple membrane filters will be discussed below.

In one version of the foregoing assembly of FIG. 5, and as mentioned, the stem 156 includes an inner diameter that is larger than an outer diameter of the filter membrane 170, and the stem 156 includes a longitudinal dimension that is larger than a longitudinal dimension of the filter membrane 170. As such, when the stem 156 and filter membrane 170 are assembled onto the connector 166, the filter membrane 170 resides entirely within (i.e., entirely inside of) the stem 156 and a gap exists between the inner sidewall of the stem 156 and the outer sidewall of the filter membrane 170. As such, fluid passing into the filter membrane 170 passes out of the plurality of pores 162 and flows without obstruction through the gap and along the inside of the stem 156 to the bladder. In some versions, the stem 156 can be a flexible tube, a rigid tube, or can include a tube with portions that are flexible and other portions that are rigid. Specifically, in some versions, a stem 156 with at least a rigid portion adjacent to the filter membrane 170 can serve to further protect the filter membrane 170 and/or prevent the filter membrane 170 from becoming pinched or kinked in a flexible tube. In other versions, such protection may not be needed or desirable. In one embodiment, the stem 156 has an internal diameter in the range of approximately 2.5 mm to approximately 8 mm, and a longitudinal dimension in the range of approximately 5 cm to approximately 30 cm. In one embodiment, the internal diameter of the stem 156 is about 0.2 to about 3 mm larger than the outer diameter of the filter membrane 170. And, the filter membrane 170 has an outer diameter in the range of approximately 2.3 mm to approximately 5 mm, a longitudinal dimension in the range of approximately 3 cm to approximately 420 cm, and a wall thickness in the range of approximately 150 µm to approximately 500 µm. Furthermore, in one version each of the plurality of pores 162 in the filter membrane 170 have a diameter less than or equal to approximately 0.2 microns. In some versions, each pore has a diameter less than or equal to a value in a range of approximately 0.1 microns to approximately 0.5 microns, for instance, approximately 0.2 to approximately 0.4 microns. In some versions, each pore has a diameter that is less than or equal to approximately 0.22 microns. In some versions, each pore has a diameter that is less than or equal to a value in a range of approximately 0.1 microns to approximately 0.2 microns. In some versions, each pore has a diameter that is less than or equal to a value in a range of approximately 0.1 microns to approximately 0.22 microns. These pore sizes coupled with the disclosed geometrical dimension of the stem 156 and filter membrane 170 ensure acceptable flow rates through the filter membrane 170 for filling the product bags with patient injectable solutions such as sterile water, sterile saline, etc. In other versions, any or all of the dimensions could vary depending on the specific application.

Suitable materials for the filter membrane 170 can include polyolefins (e.g., PE, PP), polyvinylidene fluoride, polymethylmethacrylate, polyacrylonitrile, polysulfone, and polyethersulfone. In some embodiments within the scope of the present disclosure, the filter 155 may be comprised of a blend of polysulfone or polyethersulfone and polyvinylpyrrolidone. In other embodiments within the scope of the present disclosure, the filter membrane 170 can include a polymer containing cationic charges, e.g. polymers bearing functional groups like quaternary ammonium groups. A suitable example for such polymers is polyethyleneimine. The filter membrane 170 may be manufactured by known techniques including, e.g., extrusion, phase inversion, spinning, chemical vapor deposition, 3D printing, etc. Suitable materials for the stem 156 include PVC, polyesters like PET, poly(meth)acrylates like PMMA, polycarbonates (PC), polyolefins like PE, PP, or cycloolefin copolymers (COC), polystyrene (PS), silicone polymers, etc.

Additional details regarding some possible versions of the filter and the specific construction of the membrane, for example, can be described in European Patent Application No. EP16152332.9, entitled FILTER MEMBRANE AND DEVICE, filed Jan. 22, 2016, and additionally in PCT/EP2017/051044, entitled FILTER MEMBRANE AND DEVICE, filed Jan. 19, 2017, the entire contents of each of which are expressly incorporated herein by reference.

Thus far, the hollow fiber membrane 170 in FIG. 5, for example, has been described as being located within the stem 156. In other embodiments, the filter 155 may include its own housing or other support structure, which is coupled to the stem 156 either in place of the connector 166 in FIG. 5 or connector 766 in FIGS. 6-10, or at a location between two portions of the stem 156.

Figure 11:
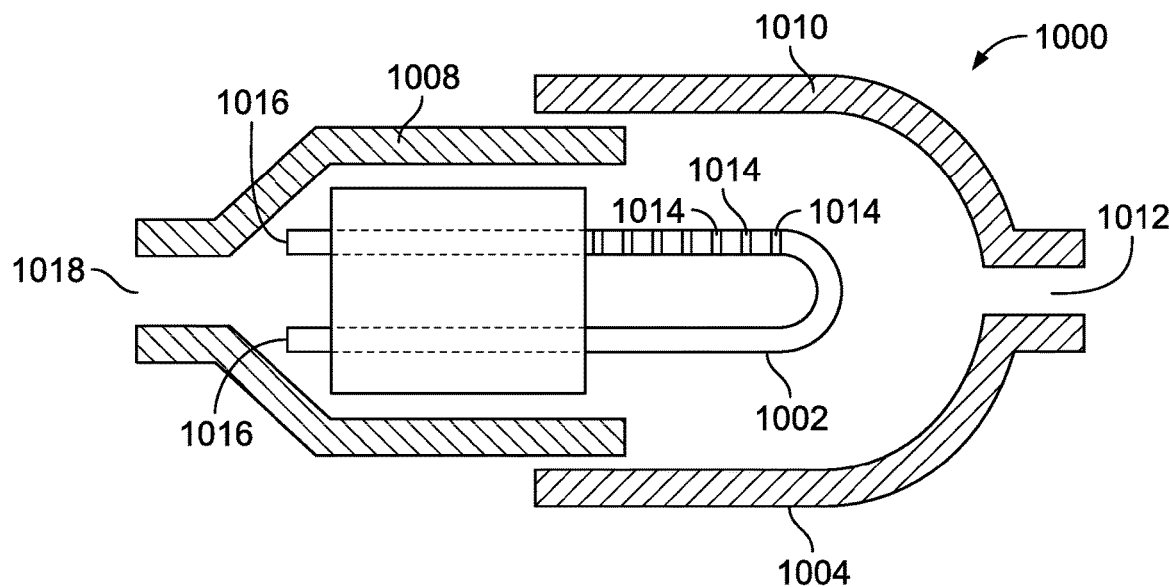
FIG. 11 is a front view of an alternative filtration device for use with any of the systems of FIGS. 1-3.

For example, FIG. 11 is a front view of a filter assembly 1000 for a product bag (not pictured) having a single U-shaped hollow fiber filter membrane 1002 contained within a filter body 1004. The filter membrane 1002 is secured to a filter membrane housing 1006 in the U-shaped configuration with an adhesive (i.e., a UV curing acrylic adhesive), an epoxy, welding, bonding, or other means. The filter membrane housing 1006 is connected to the filter body 1004 at an outlet portion 1008 of the filter body 1004. An inlet portion 1010 is sealably connected to the outlet portion 1008 of the filter body 1004 at a joint or other seam. The inlet portion 1010 of the filter body 1004 has an inlet 1012 by which a pharmaceutical fluid may enter the filter assembly 1000. The mixture from the mixing container 202 then enters the filter membrane 1002 through a plurality of pores 1014, travels through the filter membrane 1002, exits the filter membrane 1002 at filter membrane outlets 1016, and exits the filter body 1004 at filter outlet 1018. The filter outlet 418 may then be connected to the product bag 206, as shown in FIGS. 1-3 and 21. In FIG. 11, the flow of fluid through the assembly 1000 has been described as moving from the inlet 1012 of the inlet portion 1010 to the outlet 1018 of the outlet portion 1008. However, the same assembly 400 could be used in the opposite direction such that fluid enters the outlet 1018 of the outlet portion 1008 and exits the inlet 1012 of the inlet portion 1010. In this alternative configuration, fluid would first enter the inlet 1018, pass into the filter membrane 1002 at the filter membrane outlets 1016, and exit through the pores 1014 and finally the inlet 1012.

Figure 12:
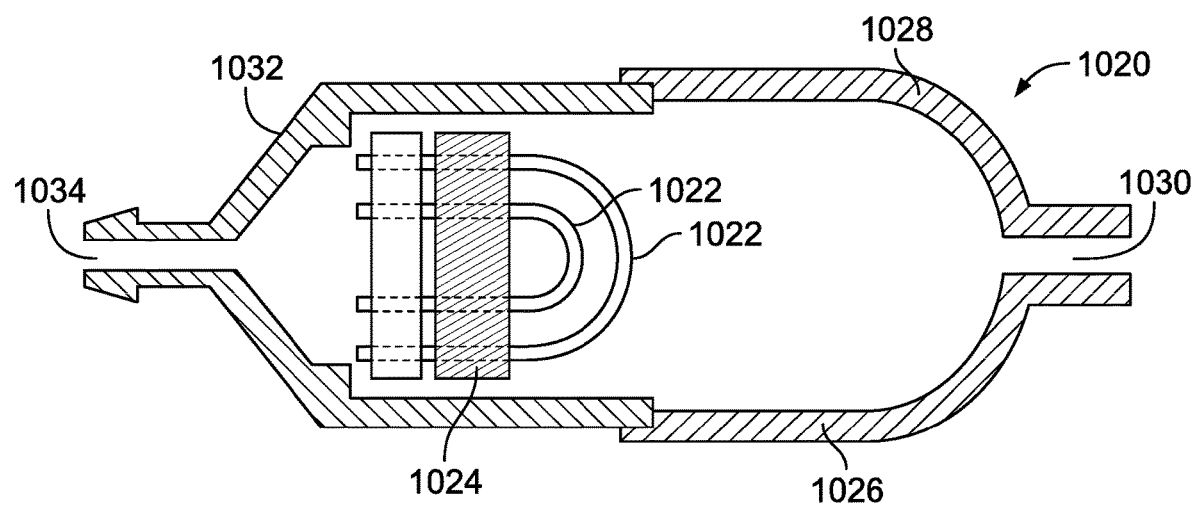
FIG. 12 is a front view of another alternative filtration device for use with any of the systems of FIGS. 1-3.

FIG. 12 is an alternate embodiment of the filter assembly 1000 depicted in FIG. 11. In FIG. 12, the filter 1020 includes two U-shaped hollow fiber filter membranes 1022 are secured to a filter membrane housing 1024 in the U-shaped configuration with an adhesive (i.e., a UV curing acrylic adhesive), an epoxy, welding, bonding, or some other means. The filter membranes 1022 and filter membrane housing 1024 are contained within a filter body 1026 having an inlet portion 1028 with inlet 1030 sealably connected to an outlet portion 1032 having filter outlet 1034. In other embodiments, a filter may include more than two U-shaped hollow fiber filter membranes arranged as depicted in FIGS. 11 and 12. In FIG. 12, like in FIG. 11, the flow of fluid through the assembly 1000 has been described as moving from the inlet portion 1028 to the outlet portion 1032. However, the same assembly 1000 could be used in the opposite direction such that fluid enters the outlet portion 1032 and exits the inlet portion 1028 as described above relative to FIG. 11.

Figure 13:
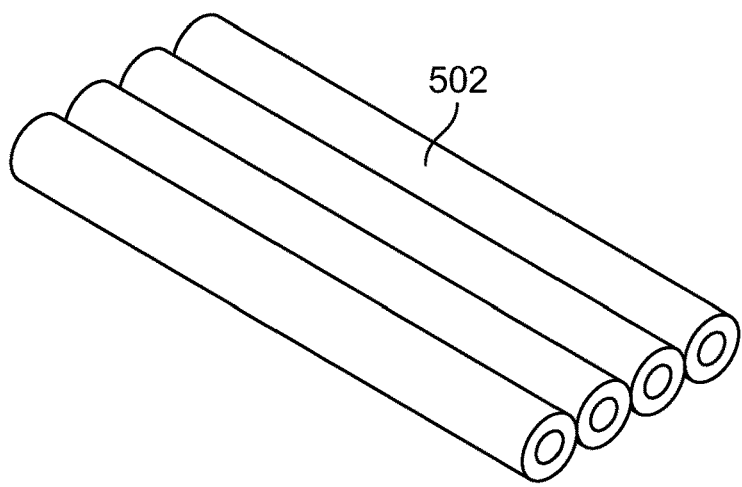
FIG. 13 is a front view of yet another filtration device for use with any of the systems of FIGS. 1-3 having a plurality of hollow fiber membranes secured side by side.

FIG. 13 is a further alternative filter assembly. Specifically, in FIG. 13, a plurality of linear membrane filters 502 are secured directly together in a parallel side-by-side configuration for what can be referred to as a fiber bundle. The filters 502 in FIG. 13 can be secured together with adhesive (i.e., a UV curing acrylic adhesive), epoxy, welding, bonding, etc. In other versions, the plurality of filters 502 can be manufactured together as one piece by way of any of the manufacturing techniques described above.

Figure 14:
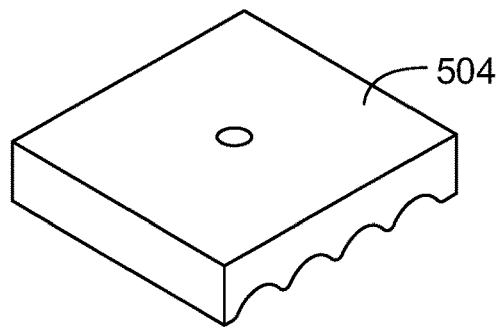
FIG. 14 is an isometric view of the securement device used for the plurality of hollow fiber membranes depicted in FIG. 13.
Figure 14:
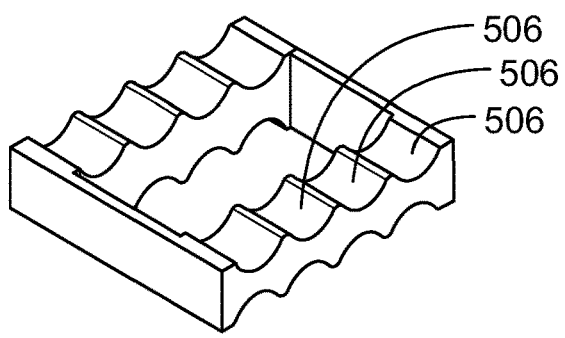
Figure 14:
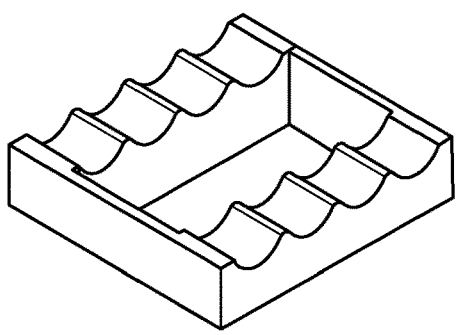

FIG. 14 provides another alternative in which a securement device 504 includes a number of blocks defining a plurality of grooves 506 identical to the number of hollow fiber membrane filters 502. The blocks of the securement device 504 may be sandwiched together and used to hold the plurality of hollow fiber membrane filters 502 in the side-by-side configuration. The securement device 504 depicted in FIG. 14 allows for two sets of the hollow fiber membrane filters 502 of FIG. 13 to be stacked relative to each other. The fiber bundle including the membrane filters 502 and the securement device 504 may be placed in a filter body, such as that discussed with respect to FIGS. 11 and 12.

Figure 15:
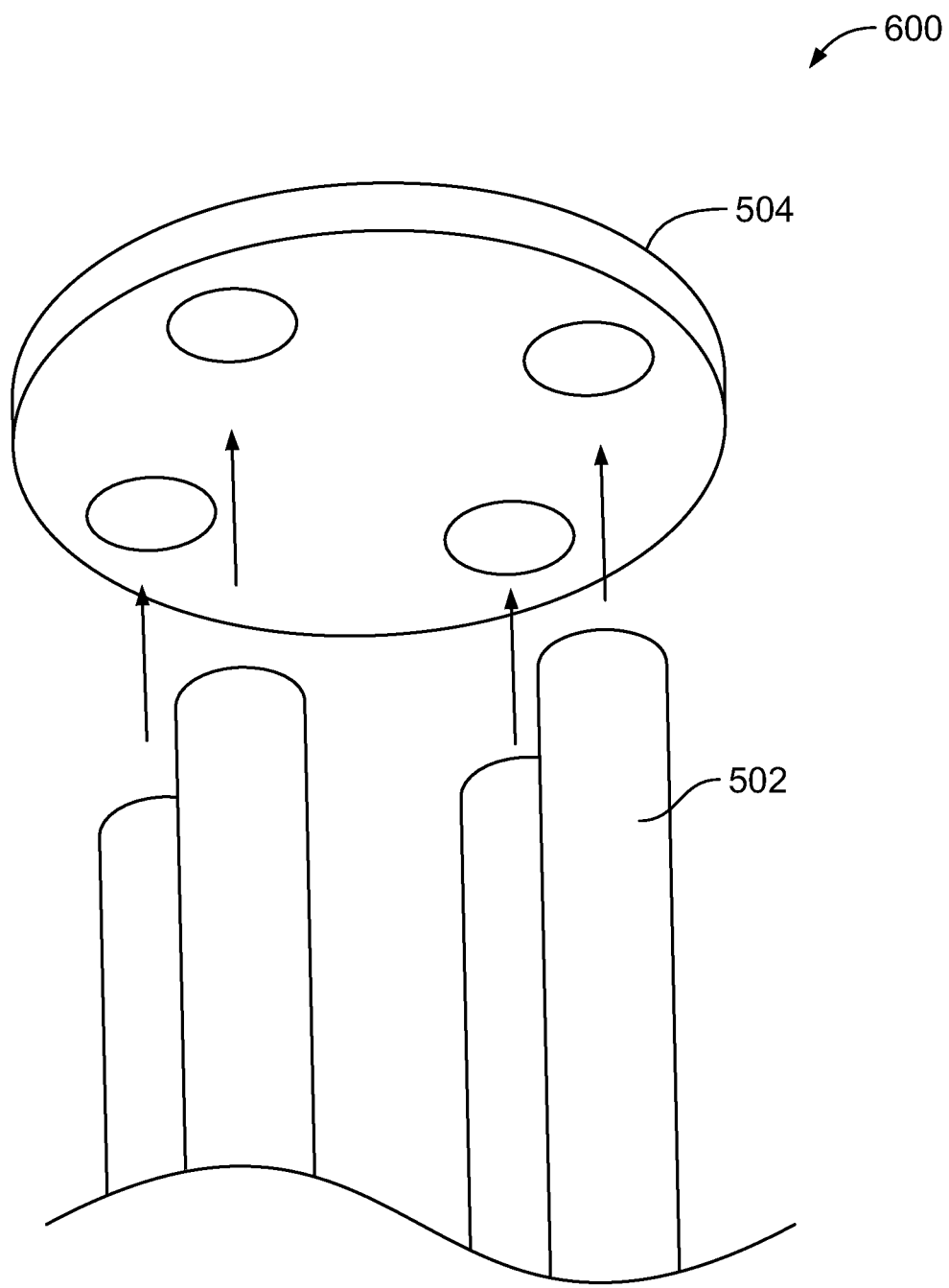
FIG. 15 is an isometric view of a fiber bundle for a product bag having a plurality of hollow fiber membranes secured in a circular holder.

FIG. 15 is an isometric view of another version of a fiber bundle 600 for a filtration device 204 having a plurality of parallel hollow fiber membrane filters 502 similar to FIGS. 13 and 14, but wherein the parallel filters 502 are arranged in a circular pattern by a circular holder 504. The fiber bundle 600 may be placed in a filter body, such as that discussed with respect to FIGS. 11 and 12.

FIGS. 16-17 and FIGS. 18-20 illustrate two additional devices for coupling fiber bundles to a stem in accordance with the present disclosure. FIGS. 16-17 discloses a connector 866 for connecting a three-fiber bundle to a stem. Specifically, the connector 866 includes a first hollow body 866a and a second hollow body 866b. The first body 866a includes a solution inlet 869, which is a stem structure, extending from a bearing plate 877. A mixture from the mixing container 202 can be fed into the fluid inlet 869 of the first hollow body 866a of the connector 866. In some versions, the fluid inlet 869 can include a Luer type fitting or other standard medical fitting.

The hollow connector 866 also includes a sealing surface 872 to which the stem 156 is attached. The sealing surface 872 in this version is a cylindrical shroud extending from the bearing plate 877 in a direction opposite to a direction of extension of the fluid inlet 869. The sealing surface 872 is disposed generally concentric with the fluid inlet 869. As such, in this embodiment, the shroud of the sealing surface 872 defines a cylindrical cavity (not shown in the drawings) for receiving a portion of the second hollow body 866b of the connector 866.

The second hollow body 866b, as depicted, includes a support plate 880 and three open outlet ends 868 extending from the support plate 880. Additionally, the support plate 880 includes an outer diameter that is essentially the same as or slightly smaller than an inner diameter of the cavity of the shroud of the sealing surface 872 such that when assembled, the support plate 880 is positioned into the cavity. In one version, the support plate 880 includes a seal member 882 around its periphery to form a fluid tight seal with the inner surface of the shroud of the sealing surface 872 when inserted into the cavity. Friction, adhesive, or some other means may retain the support plate 880 in connection with the shroud of the sealing surface 872.

As mentioned, the second body 866b includes three open outlet ends 868 extending from the support plate 880. Each open outlet end 868 is adapted to be sealingly connected to an open inlet end 160 of one of three filters 155. The connection may be achieved by gluing open inlet ends 160 of the filters 155 to the open outlet ends 868 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet ends 868 of the connector 866 comprises a hollow cylindrical member that fits inside of and is fixed to the open inlet ends 160 of the filters 155. As such, an outer diameter of the open outlet ends 868 is substantially similar to or slightly smaller than an inner diameter of the open inlet ends 160 of the filters 155. In some versions, the filters 155 may be welded to the open outlet ends 868 of the connector 866 by, for example, heat welding (e.g., introducing a hot conical metal tip into the open inlet ends 150 of the filters 155 to partially melt it), laser welding if the hollow connector 866 is made from a material that absorbs laser radiation, mirror welding, ultrasound welding, and friction welding. Alternately, the filters 155 may be inserted into a mold, and a thermoplastic polymer may be injection-molded around it to form the hollow connector 866. Other designs and configurations for connecting the filters 155 to the open outlet ends 868 are intended to be within the scope of the present disclosure.

Finally, as with previously described embodiments, the sealing surface 872 of the connector 866 can be received by the stem 156 such that the stem 156 extends therefrom to surround and protect the filters 155 without contacting the surfaces 164 of the filters 155. The stem 156 can be fixed to the sealing surface 872 with adhesive (e.g., a UV curing acrylic adhesive), epoxy, welding, bonding, etc. The stem 156 receives the pharmaceutical solution after it passes through the pores 162 in the filter 155. From there, the now filtered solution passes into the bladder 152 in the same manner described above with respect to FIGS. 3-5.

Figure 18:
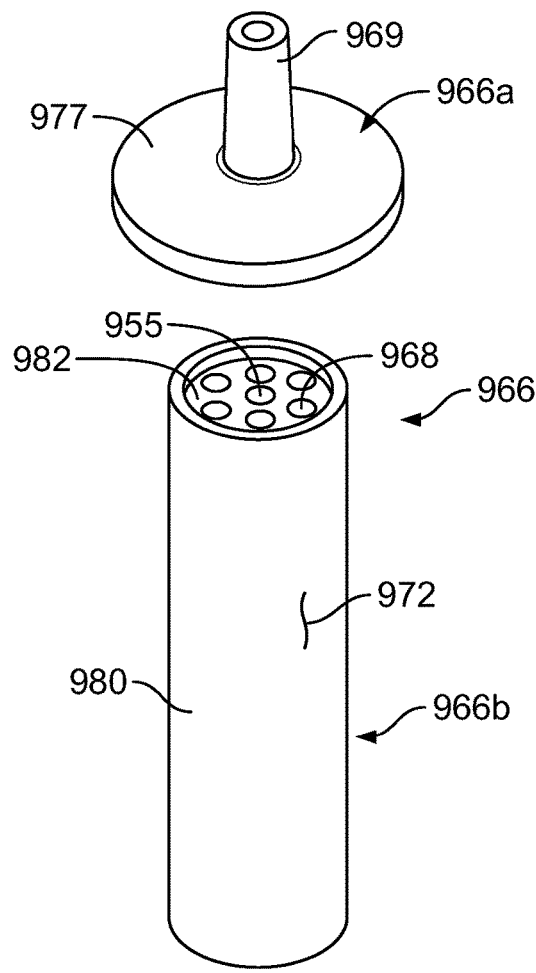
FIG. 18 is a exploded perspective view of another alternative connector for use with a seven-filter filter bundle.
Figure 19:
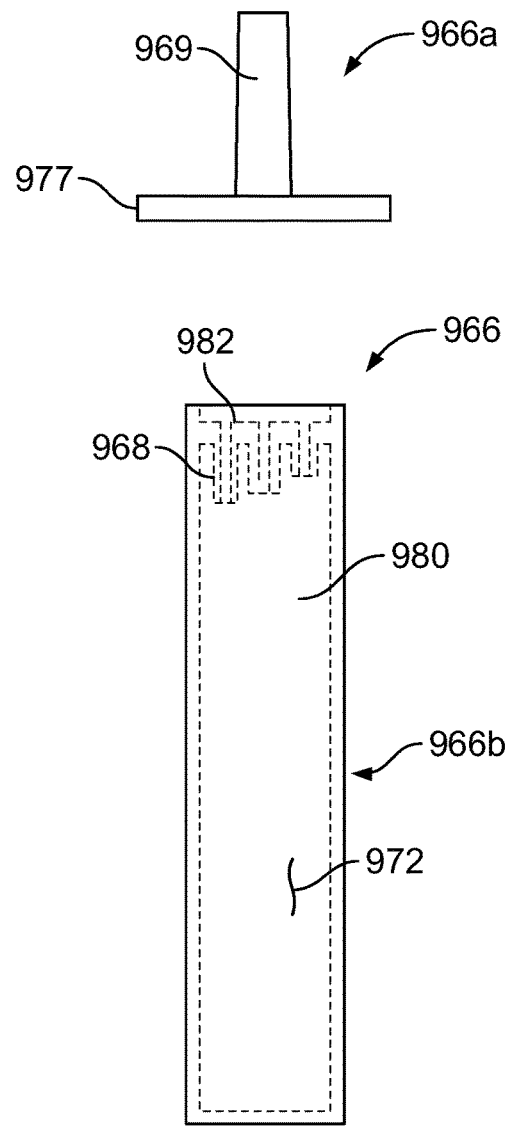
FIG. 19 is a side exploded view of the connector of FIG. 18.
Figure 20:
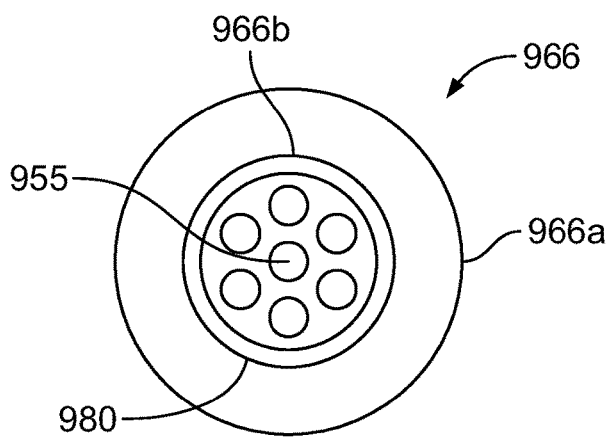
FIG. 20 is a bottom view of the connector of FIG. 19.

FIGS. 18-20 discloses a connector 966 for connecting a seven-fiber bundle to a stem. Specifically, the connector 966 includes a first hollow body 966a and a second hollow body 966b that can be connected to the first hollow body 966a with an adhesive or via other means. The first body 966a includes a solution inlet 969, which is a stem structure, extending from a bearing plate 977. A mixture from the mixing container 202 can be fed into the fluid inlet 969 of the first hollow body 966a of the connector 966. In some versions, the fluid inlet 969 can include a Luer type fitting or other standard medical fitting.

The second hollow body 966b, as depicted, includes a hollow cylindrical support collar 980 in which seven hollow fiber membrane filters 955 can be disposed parallel to each other, as shown in FIGS. 18 and 20. In one version, the support collar 980 can include a support plate 982 carrying seven open outlet ends 968 extending into the collar 980 for connecting to the filters 955 in a manner similar to that described above regarding FIGS. 16-17. The connection may be achieved by gluing the filters 955 to the open outlet ends 968 with, for example, an epoxy resin, a polyurethane resin, a cyanoacrylate resin, a UV curing acrylic adhesive, or a solvent for the material of the hollow connector 966 such as cyclohexanone. In the version depicted, the stem structure of the open outlet ends 868 of the connector 866 comprises a hollow cylindrical member that fits inside of and is fixed to the filters 955. As such, a diameter of the open outlet ends 968 is substantially similar to or slightly smaller than an inner diameter of the filters 955. In some versions, the filters 955 may be welded to the open outlet ends 968 of the connector 966 by, for example, heat welding (e.g., introducing a hot conical metal tip into the filters 955 to partially melt it), laser welding if the hollow connector 966 is made from a material that absorbs laser radiation, mirror welding, ultrasound welding, and friction welding. Alternately, the filters 955 may be inserted into a mold, and a thermoplastic polymer may be injection-molded around it to form the hollow connector 966. Other designs and configurations for connecting the filters 955 to the open outlet ends 968 are intended to be within the scope of the present disclosure.

Finally, the collar 980 of this embodiment includes a sealing surface 972 that can be received by the stem 156 such that the stem 156 extends therefrom. The stem 156 can be fixed to the sealing surface 972 with adhesive (e.g., a UV curing acrylic adhesive), epoxy, welding, bonding, etc. The stem 156 receives the mixture after it passes through the pores 162 in the filters 955. From there, the now sterilized passes into the product bag 206 in the same manner described above with respect to any of FIGS. 1-5.

From the foregoing, it can be seen that various filtering arrangements can serve the principles of the present disclosure including introducing a reconstituted to the product bag in a sterilized manner. And while the filtration device 204 throughout the disclosure has been described as including a hollow fiber filter or a plurality of hollow fiber filters, in other versions of the disclosure the filtration device 204 can include other forms of filter assemblies including, for example, a flat filter disposed within a rectangular, square or box-like filter housing. The flat filter could have any of the same characteristics as the hollow fiber filter described herein, only its geometrical shape and configuration would be different.

While certain representative versions of the claimed subject matter have been described herein for purposes of illustrating the invention, it will be apparent to those skilled in the art that various changes in the devices and methods disclosed may be made without departing from the spirit and scope of the invention, which is defined by the following claims and is not limited in any manner by the foregoing description.

The invention claimed is:

1. A system for reconstituting and sterilizing a concentrate, comprising:
a mixing container having an inlet port and outlet port in fluid communication with a mixing chamber disposed between the inlet port and the outlet port, the mixing chamber adapted to contain a product concentrate;
a filtration device having an inlet and an outlet, the inlet of the filtration device coupled to the outlet port of the mixing container, the filtration device comprising a filter membrane with a nominal pore size in a range of approximately 0.1 μm to approximately 0.5 μm; and
a product bag having an inlet port coupled to the outlet of the filtration device, the product bag having a bladder defining an empty sterile chamber for receiving sterilized and reconstituted product resulting from mixing a pharmaceutical fluid with a product concentrate in the mixing chamber to obtain a mixture then introduced through the filtration device to obtain the reconstituted and sterilized product, wherein the mixing container comprises a vial with a single open end, and the system further comprises a vial adaptor defining the inlet port and outlet port, the vial adaptor further defining a mixing port coupled to the single open end of the vial.

2. The system of claim 1, wherein the vial adaptor further comprises a first conduit establishing fluid communication between the inlet port and the mixing port, and a second conduit establishing fluid communication between the mixing port and the outlet port.

3. The system of claim 2, wherein each of the first and second conduits includes a terminal end that is disposed within the vial, the terminal end of the first conduit extending further into the vial than the second terminal end.

4. The system of claim 1,
further comprising a syringe with a delivery end adapted to be coupled to the outlet of the filtration device, the syringe having a syringe barrel defining a reservoir, a plunger, and a stopper slidably disposed in the reservoir, the reservoir defining an empty sterile chamber for receiving the reconstituted and sterilized product from the outlet of the filtration device.

5. The system of claim 1, wherein the filter membrane is shaped as (a) a hollow fiber with a wall and pores residing in the wall of the fiber, or (b) a flat filter disposed within a rectangular, square or box-like filter housing, the flat filter having a wall and pores residing in the wall.

6. The system of claim 1, wherein the filtration device comprises a stem and the filter membrane is disposed in line with the stem, wherein the stem defines a seal-and-cut area between the filter membrane and the inlet port of the product bag, the seal-and-cut area adapted to allow the stem to be sealed and cut to close the inlet port of the product bag.

7. The system of claim 1, wherein the filter membrane includes an inlet end and an outlet end, wherein the outlet end is sealed and the inlet end is an open inlet.

8. The system of claim 6, wherein the stem is one of a flexible stem or a rigid stem.

9. The system of claim 1, wherein the filter membrane has a nominal pore size in a range of approximately 0.1 μm to approximately 0.22 μm.

10. A system for reconstituting a non-sterile concentrate, comprising:
a mixing container having an inlet port and outlet port in fluid communication with a non-sterile mixing chamber disposed between the inlet port and the outlet port;
a non-sterile product concentrate disposed in the mixing chamber; and
a filtration device having an inlet and an outlet, the inlet of the filtration device coupled to the outlet port of the mixing container, the filtration device comprising a filter membrane disposed between the inlet and outlet of the filtration device and having a nominal pore size in a range of approximately 0.1 μm to approximately 0.5 μm, for producing sterilized and reconstituted product resulting from mixing a pharmaceutical fluid with the non-sterile product concentrate in the mixing chamber to obtain a non-sterile mixture then introduced through the filtration device to obtain the reconstituted and sterilized product, wherein the mixing container comprises a vial with a single open end, and the system further comprises a vial adaptor defining the inlet port and outlet port, the vial adaptor further defining a mixing port coupled to the single open end of the vial.

11. The system of claim 10, wherein the vial adaptor further comprises a first conduit establishing fluid communication between the inlet port and the mixing port, and a second conduit establishing fluid communication between the mixing port and the outlet port.

12. The system of claim 1, wherein the filter membrane has a wall thickness in the range of approximately 150 μm to approximately 500 μm.

13. The system of claim 1, wherein the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

14. The system of claim 1, wherein the filter membrane includes at least one U-shaped hollow fiber filter membrane secured in a U-shaped configuration by a filter membrane housing contained within a filter body.

15. The system of claim 1, wherein the filter membrane comprises a plurality of parallel hollow fiber membrane filters secured in a side-by-side configuration.

16. The system claim 1, wherein the filter membrane comprises a plurality of parallel hollow fiber membrane filters arranged in a circular pattern.

17. The system of claim 1, wherein the product bag further comprises an administration port separate from the inlet port of the product bag for facilitating administration of the reconstituted and sterilized product to a patient.

18. The system of claim 1, wherein the filter membrane is made of at least one of the following materials: a polyolefin, polyvinylidene fluoride, polymethylmethacrylate, polyacrylonitrile, polysulfone, polyethersulfone, and a polymer containing cationic charges.

19. The system of claim 1, wherein the stem is made of at least one of the following materials: PVC, PET, a poly(meth)acrylate, a polycarbonate, a polyolefin, a cycloolefin copolymer, polystyrene, or a silicone polymer.

20. The system of claim 11, wherein each of the first and second conduits includes a terminal end that is disposed within the vial, the terminal end of the first conduit extending further into the vial than the second terminal end.

* * * * *